United States Patent
Wang et al.

(10) Patent No.: US 9,586,957 B2
(45) Date of Patent: Mar. 7, 2017

(54) 2-KETO AMIDE DERIVATIVES AS HIV ATTACHMENT INHIBITORS

(71) Applicant: ViiV HEALTHCARE UK (NO.5) LIMITED, Brentford, Middlesex (GB)

(72) Inventors: Tao Wang, Farmington, CT (US); Zhiwei Yin, Glastonbury, CT (US); Zhongxing Zhang, Madison, CT (US); John A. Bender, Middletown, CT (US); Barry L. Johnson, Newark, DE (US); John F. Kadow, Wallingford, CT (US); Nicholas A. Meanwell, East Hampton, CT (US)

(73) Assignee: ViiV Healthcare UK (No.5) Limited, Brentford, Middlesex (GB)

( * ) Notice: Subject to any disclaimer, the term of this patent is extended or adjusted under 35 U.S.C. 154(b) by 0 days.

(21) Appl. No.: 14/779,648

(22) PCT Filed: Mar. 25, 2014

(86) PCT No.: PCT/US2014/031697
§ 371 (c)(1),
(2) Date: Sep. 24, 2015

(87) PCT Pub. No.: WO2014/160692
PCT Pub. Date: Oct. 2, 2014

(65) Prior Publication Data
US 2016/0052924 A1    Feb. 25, 2016

Related U.S. Application Data

(60) Provisional application No. 61/805,642, filed on Mar. 27, 2013.

(51) Int. Cl.
| | | |
|---|---|---|
| A61K 31/55 | (2006.01) |
| C07D 471/04 | (2006.01) |
| A61K 45/06 | (2006.01) |
| A61K 31/437 | (2006.01) |
| C07D 401/06 | (2006.01) |
| A61K 31/4545 | (2006.01) |
| A61K 31/454 | (2006.01) |
| C07D 519/00 | (2006.01) |

(52) U.S. Cl.
CPC .......... *C07D 471/04* (2013.01); *A61K 31/437* (2013.01); *A61K 31/454* (2013.01); *A61K 31/4545* (2013.01); *A61K 31/55* (2013.01); *A61K 45/06* (2013.01); *C07D 401/06* (2013.01); *C07D 519/00* (2013.01)

(58) Field of Classification Search
CPC .. C07D 471/04; C07D 519/00; A61K 31/496; A61K 45/06; A61K 31/519; A61K 31/551
USPC ...................................................... 546/113
See application file for complete search history.

(56) References Cited

U.S. PATENT DOCUMENTS

| | | | | |
|---|---|---|---|---|
| 3,686,213 | A * | 8/1972 | Poletto .................... | C07C 46/06 514/869 |
| 3,821,387 | A * | 6/1974 | Welstead ............... | A61K 31/00 514/323 |
| 5,849,764 | A * | 12/1998 | Goulet ................. | C07D 209/16 514/247 |
| 6,469,006 | B1 * | 10/2002 | Blair .................... | C07D 209/12 514/246 |
| 6,476,034 | B2 * | 11/2002 | Wang ................... | A61K 31/495 514/253.04 |
| 6,825,201 | B2 * | 11/2004 | Wang ................... | C07D 209/08 514/252.13 |
| 7,037,913 | B2 * | 5/2006 | Wang ................... | C07D 215/14 514/253.05 |
| 7,087,610 | B2 * | 8/2006 | Wang ................... | A61K 31/496 514/248 |
| 7,183,284 | B2 * | 2/2007 | Kadow ............... | C07D 471/04 514/252.12 |
| 7,348,337 | B2 * | 3/2008 | Wang ................... | C07D 401/06 514/300 |
| 7,354,924 | B2 * | 4/2008 | Wang ................... | A61K 31/496 514/241 |
| 7,449,476 | B2 * | 11/2008 | Ruediger ............. | C07D 519/00 514/292 |
| 7,501,420 | B2 * | 3/2009 | Wang ................... | A61K 31/496 514/253.04 |
| 7,531,552 | B2 * | 5/2009 | Kadow ............... | C07D 403/12 514/300 |
| 7,662,823 | B2 * | 2/2010 | Wang ................... | A61K 31/496 514/253.04 |

(Continued)

OTHER PUBLICATIONS

Helsley; Journal of Medicinal Chemistry, 1978, 21, 309-312.*
Allen; Journal of Medicinal Chemistry, 1973, 16, 949-951.*
Welstead; Journal of Medicinal Chemistry, 1967, 10, 1015-1021.*
Chemical Abstracts STN Registry Database Record for RN 18175-01-4 entered on Nov. 16, 1984.*
Chemical Abstracts STN Registry Database Record for RN 1423441-67-1 entered on Mar. 14, 2013.*
Chemical Abstracts STN Registry Database Record for RN 1421513-82-7 entered on Feb. 20, 2013.*

(Continued)

*Primary Examiner* — Noble Jarrell
*Assistant Examiner* — Daniel Carcanague
(74) *Attorney, Agent, or Firm* — Robert H. Brink; R. Steve Thomas; Edward R. Gimmi

(57) ABSTRACT

Compounds of Formula I, including pharmaceutically acceptable salts thereof: I useful as HIV attachment inhibitors.

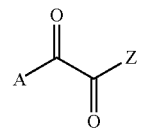

6 Claims, No Drawings

(56) References Cited

U.S. PATENT DOCUMENTS

| | | | | |
|---|---|---|---|---|
| 7,714,019 B2* | 5/2010 | Kadow | C07D 403/12 | 514/414 |
| 7,745,625 B2* | 6/2010 | Ueda | C07D 471/04 | 544/362 |
| 7,776,863 B2* | 8/2010 | Lin | A61K 31/496 | 514/183 |
| 7,807,671 B2* | 10/2010 | Wang | C07D 403/12 | 514/234.5 |
| 7,807,676 B2* | 10/2010 | Wang | C07D 403/12 | 514/252.02 |
| 7,902,204 B2* | 3/2011 | Bender | C07D 487/04 | 514/265.1 |
| 7,915,283 B2* | 3/2011 | Wang | C07D 401/06 | 514/300 |
| 7,960,406 B2* | 6/2011 | Wang | C07D 471/04 | 514/300 |
| 8,124,615 B2* | 2/2012 | Wang | C07D 471/04 | 514/300 |
| 8,168,615 B2* | 5/2012 | Ueda | C07D 471/04 | 514/81 |
| 8,242,124 B2* | 8/2012 | Regueiro-Ren | C07D 471/04 | 514/264.1 |
| 8,450,361 B2* | 5/2013 | Wang | A61K 31/437 | 514/254.09 |
| 8,461,333 B2* | 6/2013 | Ueda | C07D 471/04 | 544/337 |
| 8,664,213 B2* | 3/2014 | Wang | C07D 471/04 | 514/210.18 |
| 8,685,982 B2* | 4/2014 | Meanwell | A61K 31/496 | 514/253.09 |
| 8,835,454 B2* | 9/2014 | Wang | C07D 519/00 | 514/299 |
| 8,871,771 B2* | 10/2014 | Ueda | C07D 471/04 | 514/253.04 |
| 8,912,195 B2* | 12/2014 | Wang | C07D 471/04 | 514/253.04 |
| 9,156,828 B2* | 10/2015 | Wang | C07D 403/12 | |
| 2007/0287712 A1* | 12/2007 | Wang | C07D 209/18 | 514/253.04 |
| 2015/0210684 A1* | 7/2015 | Wang | C07D 401/06 | 514/278 |
| 2016/0052924 A1* | 2/2016 | Wang | C07D 471/04 | 514/210.18 |

OTHER PUBLICATIONS

Chemical Abstracts STN Registry Database Record for RN 1294085-57-6 entered on May 13, 2011.*
Chemical Abstracts STN Registry Database Record for RN 1210954-28-1 entered on Mar. 17, 2010.*
Chemical Abstracts STN Registry Database Record for RN 1210444-74-8 entered on Mar. 16, 2010.*
Chemical Abstracts STN Registry Database Record for RN 1209150-20-8 entered on Mar. 12, 2010.*
Chemical Abstracts STN Registry Database Record for RN 1208686-99-0 entered on Mar. 11, 2010.*
Nowicka-Sans; Antimicrob. Agents Chemother 2012, 56, 3498-3507.*
Hanna; Antimicrob. Agents Chemother 2011, 55, 722-2288.*
Wang; Bioorganic and Medicinal Chemistry Letters 2009, 19, 5140-5145.*
Chen; European Journal of Medicinal Chemistry 2011, 46, 4924-4936.*

* cited by examiner

2-KETO AMIDE DERIVATIVES AS HIV ATTACHMENT INHIBITORS

CROSS REFERENCE TO RELATED APPLICATION

This application claims the priority of U.S. Provisional Application Ser. No. 61/805,642 filed Mar. 27, 2013 which is herein incorporated by reference in its entirety.

FIELD OF THE INVENTION

This invention provides compounds having drug and bio-affecting properties, their pharmaceutical compositions and methods of use. In particular, the invention herein is directed to 2-keto amide derivatives as HIV attachment inhibitors that possess unique antiviral activity, as well as to methods for making these compounds, and to compositions containing these compounds.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), tenofovir disoproxil fumarate salt (or VIREAD®), emtricitabine (or FTC—EMTRIVA®); non-nucleoside reverse transcriptase inhibitors: nevirapine (or VIRAMUNE®), delavirdine (or RESCRIPTOR®), efavirenz (or SUSTIVA®), etravirine (INTELENCE®) and rilpivirine (EDURANT®), and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®), and integrase inhibitors such as raltegravir (ISENTRESS®), and entry inhibitors such as enfuvirtide (T-20) (FUZEON®) and maraviroc (SELZENTRY®). Several single pill combinations have been also approved, which include COMBIVIR® (contains lamivudine and zidovudine), TRIZIVIR® (contains abacavir, zidovudine, and lamivudine), EPZICOM® (contains abacavir and lamivudine), TRUVADA® (contains tenofovir disoproxil fumarate and emtricitabine), ATRIPLA® (contains efavirenz, emtricitabine and tenofovir disoproxil fumarate) and COMPLERA® (contains emtricitabine, rilpivirine, and tenofovir disoproxil fumarate).

Each of these drugs can only transiently restrain viral replication if used alone. However, when used in combination, these drugs have a profound effect on viremia and disease progression. In fact, significant reductions in death rates among AIDS patients have been documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g., most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a novel subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. A disclosure describing indoles of which the structure shown below for BMS-705 is representative, has been disclosed in U.S. Pat. No. 6,469,006 (Antiviral Indoleoxoacetyl Piperazine Derivatives).

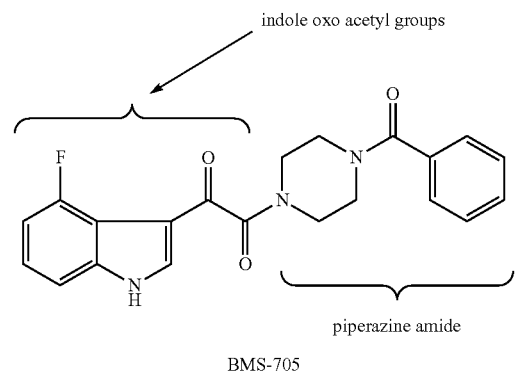 [SMILES: O=C(C(=O)N1CCN(C(=O)c2ccccc2)CC1)c1c[nH]c2cccc(F)c12]

BMS-705

Two other compounds, referred to in the literature as BMS-806 and BMS-043 have been described in both the academic and patent art:

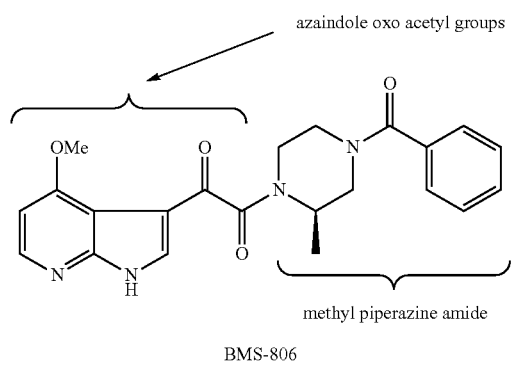

BMS-806

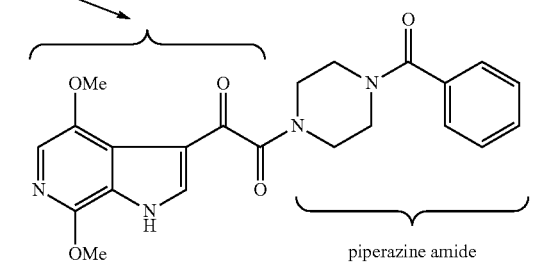

BMS-043

Some description of their properties in human clinical trials has been disclosed in the literature.

It should be noted that in all three of these structures, a piperazine amide (in these three structures a piperazine phenyl amide) is present and this group is directly attached to an oxoacetyl moiety. The oxoacetyl group is attached at the 3-position of 4-fluoro indole in BMS-705 and to the 3 position of substituted azaindoles in BMS-806 and BMS-043.

In an effort to obtain improved anti-HIV compounds, later publications described in part, modified substitution patterns on the indoles and azaindoles. Examples of such efforts include: (1) novel substituted indoleoxoacetic piperazine derivatives, (2) substituted piperazinyloxoacetylindole derivatives, and (3) substituted azaindoleoxoacetic piperazine derivatives.

Replacement of these groups with other heteroaromatics or substituted heteroaromatics or bicyclic hydrocarbons was also shown to be feasible. Examples include: (1) indole, azaindole and related heterocyclic amidopiperazine derivatives; (2) bicycle[4.4.0] antiviral derivatives; and (3) diazaindole derivatives.

A select few replacements for the piperazine amide portion of the molecules have also been described in the art and among these examples are (1) some piperidine alkenes; (2) some pyrrolidine amides; (3) some N-aryl or heteroaryl piperazines; (4) some piperazinyl ureas; and (5) some carboline-containing compounds.

Method(s) for preparing prodrugs for this class of compounds are disclosed in Prodrugs of Piperazine and Substituted Piperidine Antiviral Agents (Ueda et al., U.S. Pat. No. 7,745,625 or WO 2005/090367 A1).

A published PCT patent application WO 2003/103607 A1 (Jun. 11, 2003) discloses an assay useful for assaying some HIV inhibitors.

Several published patent applications describe combination studies with piperazine benzamide inhibitors, for example, U.S. Publication No. 2005/0215543 (WO 2005/102328 A1), U.S. Publication No. 2005/0215544 (WO 2005/102391 A1), and U.S. Pat. No. 7,776,863 (WO 2005/102392 A2).

A publication on new compounds in this class of attachment inhibitors (Wang, J. et al., Org. Biol. Chem., 3:1781-1786 (2005)) and a patent application on some more remotely related compounds have appeared in WO 2005/016344.

Published patent applications WO 2005/016344 and WO 2005/121094 also describe piperazine derivatives which are HIV inhibitors. Other references in the HIV attachment area include U.S. Pat. Nos. 7,851,476, 7,396,830 and 7,504,399, WO 2007/103456, as well as U.S. Pat. Nos. 7,348,337 and 7,354,924. A literature reference is J. Med. Chem., 50:6535 (2007).

What is therefore needed in the art are new HIV attachment inhibitor compounds, and compositions thereof, which are efficacious against HIV infection.

Of particular interest are new 2-keto amide derivatives as HIV attachment inhibitor compounds, described herein. The compounds of the present invention are 2-keto amide derivatives, which are believed to be structurally distinct from the piperazine aryl amide HIV attachment inhibitors set forth in the existing literature.

SUMMARY OF THE INVENTION

The present invention provides compounds of Formula I below, the pharmaceutically acceptable salts and/or solvates (e.g., hydrates) thereof, their pharmaceutical formulations, and their use in patients suffering from or susceptible to a virus such as HIV. The compounds of Formula I, their pharmaceutically acceptable salts and/or solvates are effective antiviral agents, particularly as inhibitors of HIV. They are useful for the treatment of HIV and AIDS.

One embodiment of the present invention is directed to one or more compounds of Formula I, including pharmaceutically acceptable salts thereof:

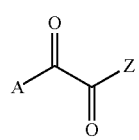

I wherein A is selected from the group consisting of:

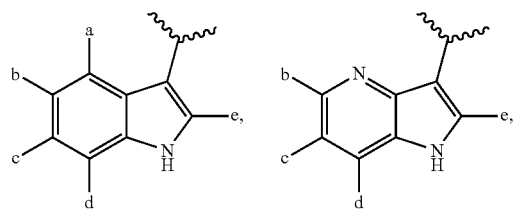

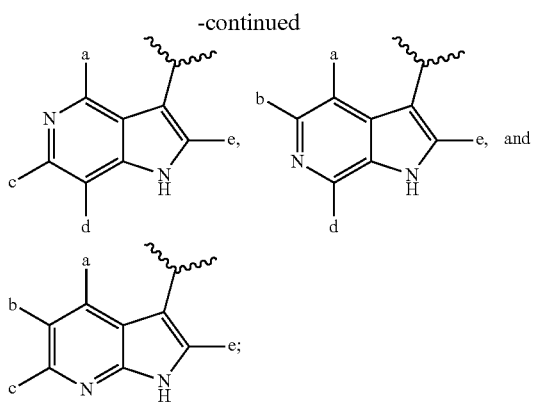

wherein a, b, c, d and e are independently selected from the group consisting of hydrogen, halogen, cyano, nitro, $COOR^{56}$, $XR^{57}$, $NA^1A^2$, $C(O)R^7$, $C(O)NR^{55}R^{56}$, B, Q, and E;

B is selected from the group consisting of —C(=$NR^{46}$)($R^{47}$), $C(O)NR^{40}R^{41}$, aryl, heteroaryl, heteroalicyclic, $S(O)_2R^8$, $S(O)_2NR^{40}R^{41}$, $C(O)R^7$, $XR^{8a}$, $(C_{1-6})$alkyl$NR^{40}R^{41}$, $(C_{1-6})$alkyl$COOR^{8b}$; wherein said aryl, heteroaryl, and heteroalicyclic are optionally substituted with one to three same or different halogens or from one to three same or different substituents selected from the group F; wherein aryl is napthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;

Q is selected from the group consisting of $(C_{1-6})$alkyl, $(C_{3-7})$cycloalkyl and $(C_{2-6})$alkenyl; wherein said $(C_{1-6})$alkyl and $(C_{2-6})$alkenyl are optionally substituted with one to three same or different halogens or from one to three same or different substituents selected from the group consisting of $C(O)NR^{55}R^{56}$, hydroxy, cyano and $XR^{57}$;

E is selected from the group consisting of $(C_{1-6})$alkyl, $(C_{3-7})$cycloalkyl and $(C_{2-6})$alkenyl; wherein said $(C_{1-6})$alkyl and $(C_{2-6})$alkenyl are independently optionally substituted with a member selected from the group consisting of phenyl, heteroaryl, SMe, SPh, —$C(O)NR^{56}R^{57}$, $C(O)R^{57}$, $SO_2(C_{1-6})$alkyl and $SO_2Ph$; wherein heteroaryl is a monocyclic system which contains from 3 to 7 ring atoms, including from 1 to 4 heteroatoms;

F is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, $(C_{1-6})$thioalkoxy, cyano, halogen, nitro, —$C(O)R^{57}$, benzyl, —$NR^{42}C(O)$—$(C_{1-6})$alkyl, —$NR^{42}C(O)$—$(C_{3-6})$cycloalkyl, —$NR^{42}C(O)$-aryl, —$NR^{42}C(O)$-heteroaryl, —$NR^{42}C(O)$-heteroalicyclic, a 4, 5, or 6 membered ring cyclic N-lactam, —$NR^{42}S(O)_2$—$(C_{1-6})$alkyl, —$NR^{42}S(O)_2$—$(C_{3-6})$cycloalkyl, —$NR^{42}S(O)2$-aryl, —$NR^{42}S(O)_2$-heteroaryl, —$NR^{42}S(O)2$-heteroalicyclic, $S(O)_2(C_{1-6})$alkyl, $S(O)_2$aryl, —$S(O)2NR^{42}R^{43}$, $NR^{42}R^{43}$, $(C_{1-6})$alkyl$C(O)NR^{42}R^{43}$, $C(O)NR^{42}R^{43}$, $NHC(O)NR^{42}R^{43}$, $OC(O)NR^{42}R^{43}$, $NHC(O)OR^{54}$, $(C_{1-6})$alkyl$NR^{42}R^{43}$, $COOR^{54}$, and $(C_{1-6})$alkyl$COOR^{54}$; wherein said $(C_{1-6})$alkyl, $(C_{3-7})$cycloalkyl, aryl, heteroaryl, heteroalicyclic, $(C_{1-6})$alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

G is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, cyano, halogen, nitro, —$C(O)R^{57}$, benzyl, —$NR^{48}C(O)$—$(C_{1-6})$alkyl, —$NR^{48}C(O)$—$(C_{3-6})$cycloalkyl, —$NR^{48}C(O)$-aryl, —$NR^{48}C(O)$-heteroaryl, —$NR^{48}C(O)$-heteroalicyclic, a 4, 5, or 6 membered ring cyclic N-lactam, —$NR^{48}S(O)_2$—$(C_{1-6})$alkyl, —$NR^{48}S(O)_2$—$(C_{3-6})$cycloalkyl, —$NR^{48}S(O)2$-aryl, —$NR^{48}S(O)_2$-heteroaryl, —$NR^{48}S(O)2$-heteroalicyclic, sulfinyl, sulfonyl, sulfonamide, $NR^{48}R^{49}$, $(C_{1-6})$alkyl$C(O)NR^{48}R^{49}$, $C(O)NR^{48}R^{49}$, $NHC(O)NR^{48}R^{49}$, $OC(O)NR^{48}R^{49}$, $NHC(O)OR^{54}$', $(C_{1-6})$alkyl$NR^{48}R^{49}$, $COOR^{54}$, and $(C_{1-6})$alkyl$COOR^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

$R^7$ is selected from the group consisting of $(C_{1-6})$alkyl, $(C_{2-6})$alkenyl, $(C_{3-7})$cycloalkyl, aryl, heteroaryl, and heteroalicyclic; wherein said aryl, heteroaryl, and heteroalicyclic are optionally substituted with one to three same or different halogens or with from one to three same or different substituents selected from the group F;

wherein for $R^7$, $R^8$, $R^{8a}$, $R^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

$R^8$ is selected from the group consisting of hydrogen, $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic; wherein said $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic are optionally substituted with one to six same or different halogens or from one to five same or different substituents selected from the group F or $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

$R^{8a}$ is a member selected from the group consisting of aryl, heteroaryl, and heteroalicyclic; wherein each member is independently optionally substituted with one to six same or different halogens or from one to five same or different substituents selected from the group F;

$R^{8b}$ is selected from the group consisting of hydrogen, $(C_{1-6})$alkyl and phenyl;

X is selected from the group consisting of $CR_1R_2$, NH or $NCH_3$, O, and S;

$R^{40}$ and $R^{41}$ are independently selected from the group consisting of (a) hydrogen; (b) $(C_{1-6})$alkyl or $(C_{3-7})$cycloalkyl substituted with one to three same or different halogens or from one to two same or different substituents selected from the group F or different functional groups: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and (c) $(C_{1-6})$alkoxy, aryl, heteroaryl or heteroalicyclic; or $R^{40}$ and $R^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is $C(O)NR^{40}R^{41}$, at least one of $R^{40}$ and $R^{41}$ is not selected from groups (a) or (b);

$R^{42}$ and $R^{43}$ are independently selected from the group consisting of hydrogen, $(C_{1-6})$alkyl, allyl, $(C_{1-6})$alkoxy, $(C_{3-7})$cycloalkyl, aryl, heteroaryl and heteroalicyclic; or $R^{42}$ and $R^{43}$ taken together with the nitrogen to which they are attached form a member selected from the group consisting of aziridine, azetidine, pyrrolidine, piperazine, 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to three same or different halogens or from one to two same or different substituents selected from the group G or different functional groups: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

$R^{46}$ is selected from the group consisting of H, phenyl, aryl, heteroaryl and $(C_{1-6})$alkyl, $OR^{57}$, and $NR^{55}R^{56}$;

$R^{47}$ is selected from the group consisting of H, amino, hydroxyl, phenyl, aryl, heteroaryl and $(C_{1-6})$alkyl;

$R^{48}$ and $R^{49}$ are independently selected from the group consisting of hydrogen, $(C_{1-6})$alkyl, phenyl, aryl and heteroaryl;

$R^{50}$ is selected from the group consisting of H, $(C_{1-6})$alkyl, $(C_{3-6})$cycloalkyl, and benzyl; wherein each of said $(C_{1-6})$alkyl, $(C_{3-7})$cycloalkyl and benzyl are optionally substituted with one to three same or different $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl $R^{54}$ is selected from the group consisting of hydrogen and $(C_{1-6})$alkyl;

$R^{54'}$ is $(C_{1-6})$alkyl;

$R^{55}$ and $R^{56}$ are independently selected from the group consisting of hydrogen and $(C_{1-6})$alkyl; and $R^{57}$ is selected from the group consisting of hydrogen, $(C_{1-6})$alkyl, aryl, heteroaryl; and $A^1$ and $A^2$ are independently selected from hydrogen, $(C_{1-6})$alkyl, aryl, heteroaryl, $SO_2D^1$, $SO_2ND^2D^3$, $COD^4$, $COCOD^4$, $COOD^4$, $COND^5D^6$, $COCOND^5D^6$, $COCOOD^4$, $C(=ND^7)D^8$, $C(=ND^9)ND^{10}D^{11}$;

$A^1$ and $A^2$ can either never connect with each other, or conjoin to form a ring structure;

$D^1$, $D^2$, $D^3$, $D^4$, $D^5$, $D^6$, $D^7$, $D^8$, $D^9$, $D^{10}$, and $D^{11}$ are each independently selected from the group consisting of H, $C_1$-$C_{50}$ alkyl, $C_3$-$C_{50}$ cycloalkyl, $C_3$-$C_{50}$ alkenyl, $C_4$-$C_{50}$ cycloalkenyl, phenyl, heteroaryl, $C_3$-$C_{50}$ amide and $C_3$-$C_{50}$ ether; heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl; provided the carbon atoms which comprise the carbon-carbon double bond of said $C_3$-$C_{20}$ alkenyl or the carbon-carbon triple bond of said $C_3$-$C_{20}$ alkynyl are not the point of attachment to the nitrogen to which $D^2$, $D^3$, $D^5$, $D^6$, $D^7$, $D^9$, $D^{10}$, and $D^{11}$ is attached; wherein said $C_1$-$C_{50}$ alkyl, $C_3$-$C_{50}$ cycloalkyl, $C_3$-$C_{50}$ alkenyl, $C_4$-$C_{50}$ cycloalkenyl, aryl, phenyl, heteroaryl, $C_3$-$C_{50}$ amide and $C_3$-$C_{50}$ ether is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide and steroid, among which ether, peroxide, thioether, secondary amine, tertiary amine, ammonium, ester, ketone, amide, amidine, oxime, hydrazine can be either acyclic or cyclic;

Z is selected from the group of:

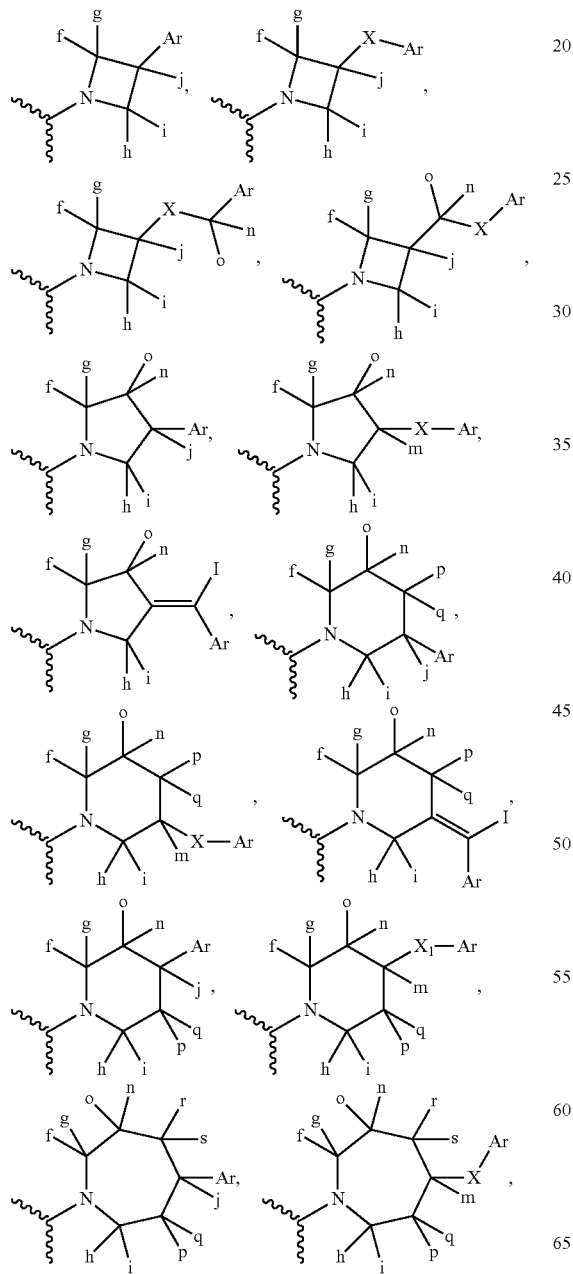

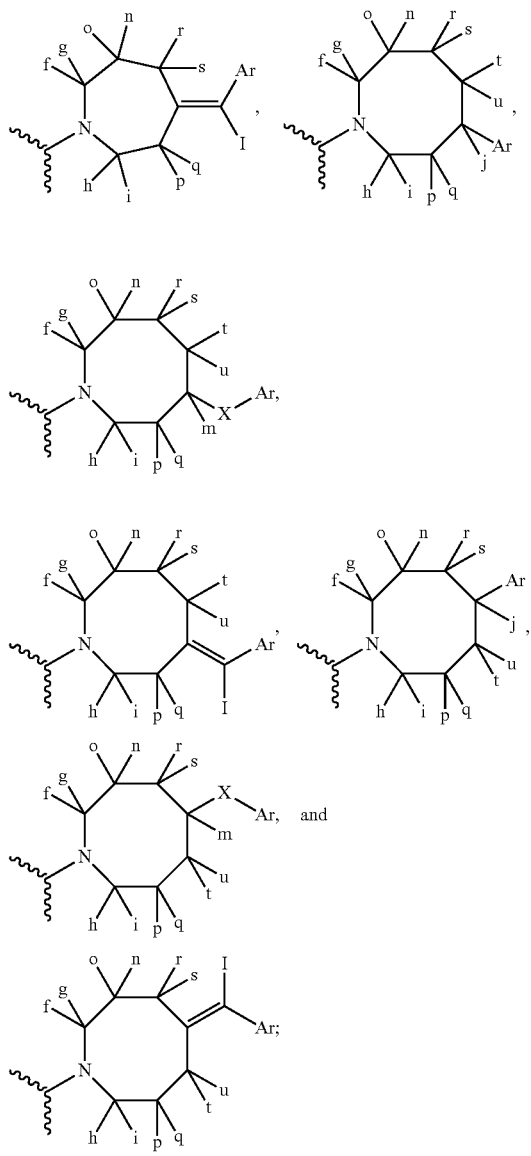

Z is also selected from the group of:

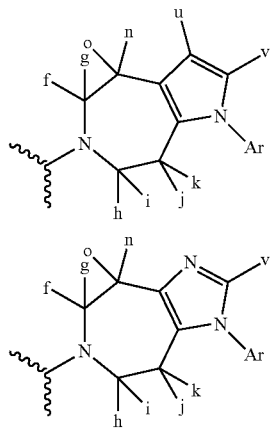

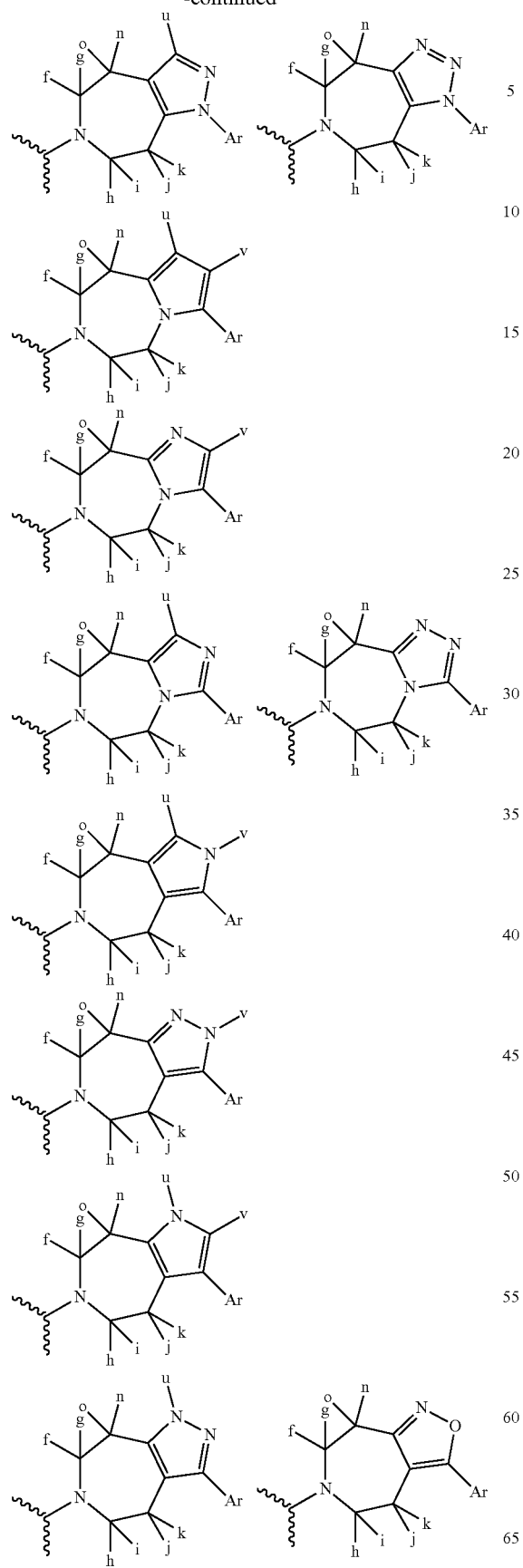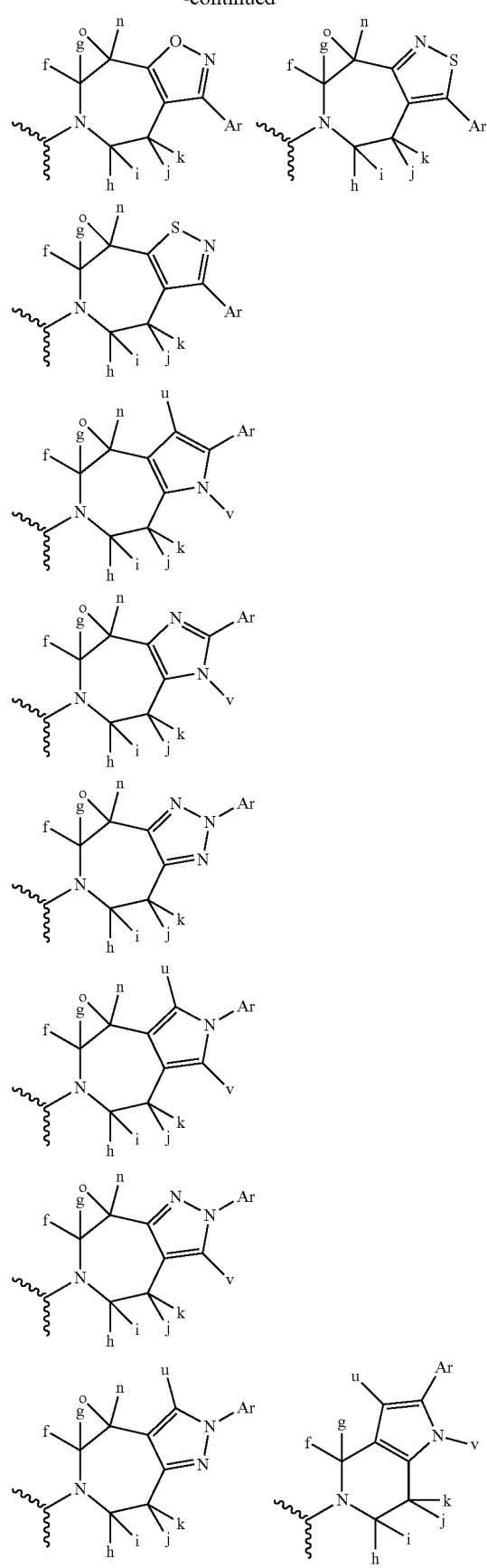

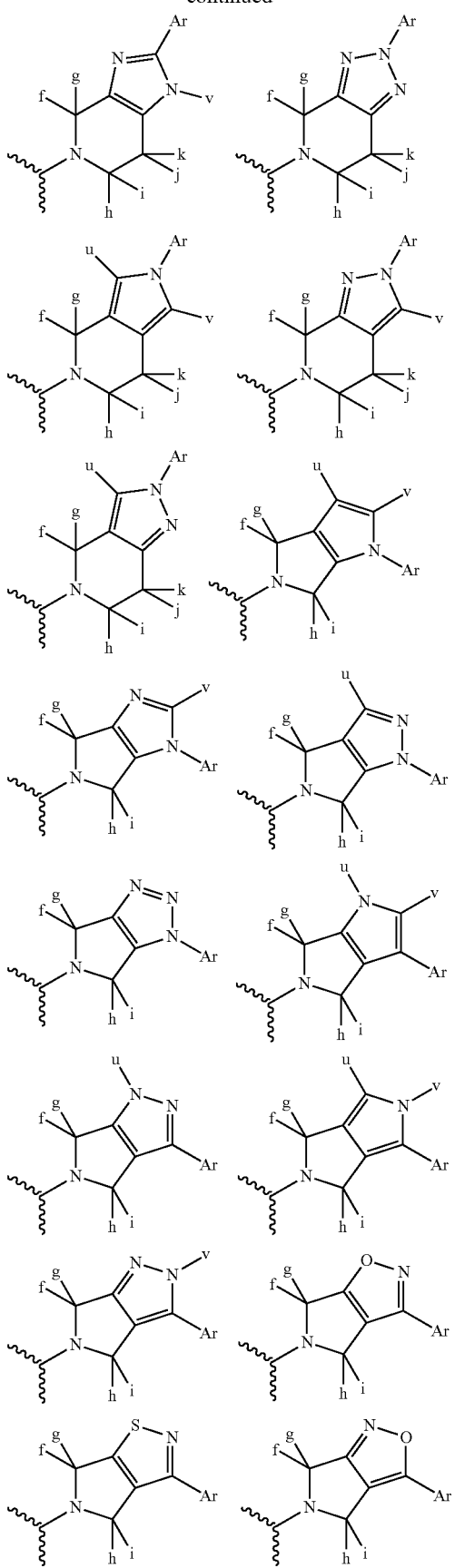
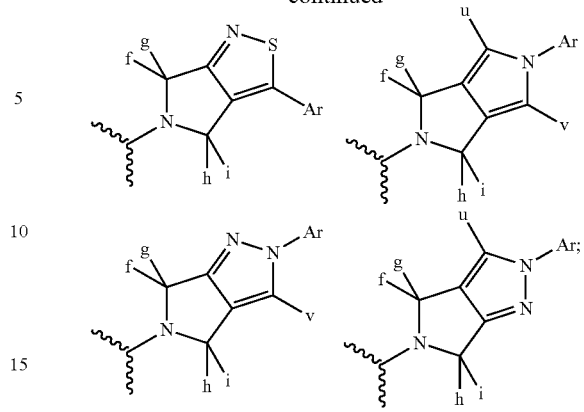

f and g are selected from the group consisting of H, $(C_1-C_4)$ alkyl, and $(C_3-C_6)$ cycloalkyl group, and wherein said alkyl or cycloalkyl group is optionally substituted with one to three substitutions selected from the group of F, OH, OR, $NR_1R_2$, COOR, and $CONR_1R_2$;

and wherein f and g can be connected by carbon, oxygen, nitrogen or sulfur atom to form a ring;

h and i are selected from the group consisting of H, $(C_1-C_4)$ alkyl, and $(C_3-C_6)$ cycloalkyl group. wherein said alkyl or cycloalkyl group is optionally substituted with one to three substitutions selected from the group of F, OH, OR, $NR_1R_2$, COOR, and $CONR_1R_2$;

and wherein h and i can be connected by a carbon, oxygen, nitrogen or sulfur atom to form a ring;

j is selected from the group consisting of H, F, $(C_1-C_4)$ alkyl, and $(C_3-C_6)$ cycloalkyl group, and wherein said alkyl or cycloalkyl group is optionally substituted with one to three substitutions selected from the group of F, OH, OR, $NR_1R_2$, COOR, and $CONR_1R_2$;

l is selected from the group consisting of hydrogen, $(C_{1-6})$ alkyl, $(C_{1-6})$alkynyl, $(C_{3-6})$ cycloalkyl, halogen, cyano, —$CONR^{32}R^{33}$, —$SO2\ R^{32}$, $COR^{32}$, $COOR^8$, tetrahydrofuryl, pyrrolidinyl, phenyl and heteroaryl; wherein said $(C_{1-6})$alkyl, $(C_{1-6})$alkynyl, phenyl and heteroaryl are each independently optionally substituted with one to three same or different members selected from the group U;

heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

m is selected from the group consisting of H, $(C_1-C_4)$ alkyl optionally substituted with one to three substitutions selected from F, OH, OR, $NR_1R_2$, COOR, $CONR_1R_2$, $(C_3-C_6)$ cycloalkyl optionally substituted with one to three substitutions selected from F, OH, OR, $NR_3R_4$, COOR, CON $R_3R_4$, OR, halogen (attached to carbon only), and Group X;

n, o, p, q, r, s, t and u are selected from the group consisting of H, F, $(C_1-C_4)$ alkyl, and $(C_3-C_6)$ cycloalkyl group, and wherein said alkyl or cycloalkyl group is optionally substituted with one to three substitutions selected from the group of F, OH, OR, $NR_1R_2$, COOR, and $CONR_1R_2$;

and wherein n, o, p, q, r, s, t and u can be connected by carbon, oxygen, nitrogen or sulfur atom to form a ring;

u and v are selected from the group consisting of H, OH, $NR_{1a}R_{2a}$, $(C_1-C_4)$ alkyl optionally substituted with one to three substitutions selected from F, OH, OR, $NR_1R_2$, COOR, $CONR_1R_2$, $(C_3-C_6)$ cycloalkyl optionally substituted with one to three substitutions selected from F, OH, OR, $NR_3R_4$, COOR, CON $R_3R_4$, OR, halogen (attached to carbon only), and Group X;

$X_1$ is selected from the group consisting of NH or $NCH_3$, O, and S;

Ar is selected from the group consisting of phenyl and heteroaryl; wherein said phenyl and heteroaryl are independently optionally substituted with one to three same or different halogens or from one to three same or different substituents selected from Group Y; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group U is selected from the group consisting of $(C_{1-6})$alkyl, $(C_{3-6})$cycloalkyl cyano, trimethylsilyl, phenyl, heteroaryl, heteroalicyclic, hydroxy, $(C_{1-6})$alkoxy, halogen, benzyl, $—NR^{42}C(O)—(C_{1-6})$alkyl, $—NR^{42}R^{43}$, $—C(O)NR^{42}R^{43}$, morpholino, nitro, $—S(C_{1-6})$alkyl, $—SPh$, $NR^{42}S(O)_2$-alkyl, piperazinyl, N-Me piperazinyl, $(CH2)_n COOR^{54}$ and $—CONR^{42}R^{43}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

Group X is selected from the group consisting of phenyl and heteroaryl; wherein said phenyl and heteroaryl are independently optionally substituted with one to three same or different halogens or from one to three same or different substituents selected from Group D; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group Y is selected from the group consisting of OH, OR, $NR_1R_2$, CN, COOR, $CONR_1R_2$, $(C_1-C_4)$ alkyl, $(C_3-C_6)$ cycloalkyl, and wherein said alkyl or cycloalkyl group is optionally substituted with one to three substitutions selected from the group of F, OH, OR, $NR_1R_2$, COOR, and $CONR_1R_2$;

R, $R_1$, $R_2$, $R_{1a}$ and $R_{2a}$ are independently H, $(C_1-C_4)$ alkyl, $(C_3-C_6)$ cycloalkyl group; wherein said alkyl or cycloalkyl group is optionally substituted with one to three substitutions selected from F, OH, OR, $NR_3R_4$, COOR, CON $R_3R_4$;

and wherein $R_1$ and $R_2$ can be connected by carbon, oxygen, nitrogen or sulfur atom to form a ring; and $R_3$ and $R_4$ are independently H, $(C_1-C_4)$ alkyl, $(C_3-C_6)$ cycloalkyl group.

Another embodiment of the present invention is directed to a method for treating mammals infected with a virus, especially wherein the virus is HIV, comprising administering to said mammal an antiviral effective amount of a compound of Formula I above, and one or more pharmaceutically acceptable carriers, excipients and/or diluents. Optionally, the compound of Formula I can be administered in combination with an antiviral effective amount of an AIDS treatment agent selected from the group consisting of: (a) an AIDS antiviral agent; (b) an anti-infective agent; (c) an immunomodulator; and (d) other HIV entry inhibitors.

Another embodiment of the present invention is directed to a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I.

The present invention is directed to these, as well as other important ends, hereinafter described.

DETAILED DESCRIPTION OF THE EMBODIMENTS

Since the compounds set forth herein may possess asymmetric centers and therefore occur as mixtures of diastereomers and enantiomers, the present invention includes the individual diastereoisomeric and enantiomeric forms of the compounds of Formula I in addition to the mixtures thereof.

Definitions

Unless otherwise specifically set forth elsewhere in the application, one or more of the following terms may be used herein, and shall have the following meanings:

The term "H" refers to hydrogen, including its isotopes.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1-C_4$fluoroalkyl" refers to F-substituted $C_1-C_4$ alkyl wherein at least one H atom is substituted with F atom, and each H atom can be independently substituted by F atom.

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and $—NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —WRY, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, 0-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane.

A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$— groups with Z as defined above.

A "trihalomethanesulfonamido" group refers to a $Z_3CS$(=O)$_2NR^x$— group with Z as defined above and $R^x$ being H or ($C_{1-6}$)alkyl.

A "sulfinyl" group refers to a —S(=O)—R" group, with R" being ($C_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-Sulfonamido" group refers to a R"S(=O)$_2$NR$_X$— group, with R$_x$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with R$^x$ and R$^y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a R$^x$OC(=S)NR$^y$— group, with R$^x$ and R$^y$ independently being H or (C$_{1-6}$)alkyl.

An "amino" group refers to an —NH$_2$ group.

A "C-amido" group refers to a —C(=O)NR$^x$N$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$)alkyl.

A "guanidino" group refers to a —R$^x$NC(=N)NR$^y$R$^{y2}$ group, with R$^x$, R$^y$, and R$^{y2}$ independently being H or (C$_{1-6}$)alkyl.

A "guanyl" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$)alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

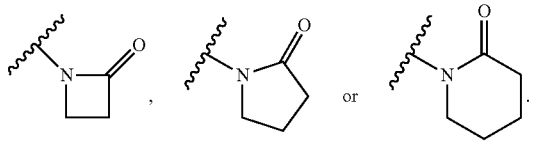 [SMILES: *N1CCC1=O ; *N1CCCC1=O ; *N1CCCCC1=O]

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfuric acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g., hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like.

As set forth above, the invention is directed to compounds of Formula I, including pharmaceutically acceptable salts thereof:

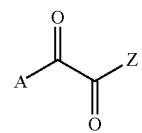

I wherein A is selected from the group consisting of:

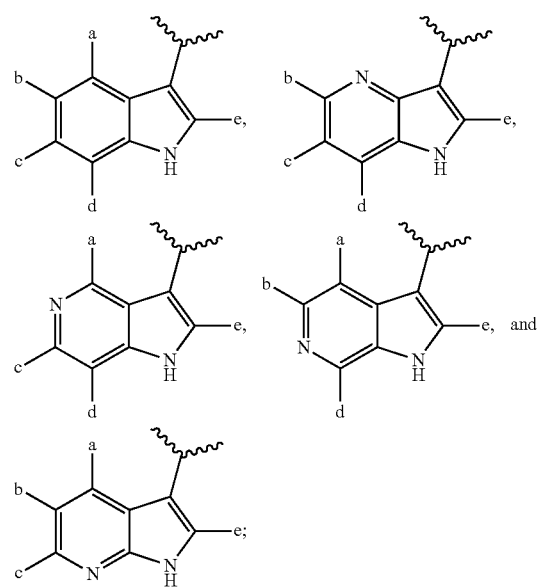

wherein
a, b, c, d and e are independently selected from the group consisting of hydrogen, halogen, cyano, nitro, COOR$^{56}$, XR$^{57}$, NA$^1$A$^2$, C(O)R$^7$, C(O)NR$^{55}$R$^{56}$, B, Q, and E;

B is selected from the group consisting of —C(=NR$^{46}$) (R$^{47}$) C(O)NR$^{40}$R$^{41}$, aryl, heteroaryl, heteroalicyclic, S(O)$_2$R$^8$, S(O)$_2$NR$^{40}$R$^{41}$, C(O)R$^7$, XR$^{8a}$, (C$_{1-6}$) alkylNR$^{40}$R$^{41}$, (C$_{1-6}$)alkylCOOR$^{8b}$; wherein said aryl, heteroaryl, and heteroalicyclic are optionally substituted with one to three same or different halogens or from one to three same or different substituents selected from the group F; wherein aryl is napthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;

Q is selected from the group consisting of (C$_{1-6}$)alkyl, (C$_{3-7}$)cycloalkyl and (C$_{2-6}$)alkenyl; wherein said (C$_{1-6}$)alkyl and (C$_{2-6}$)alkenyl are optionally substituted with one to three same or different halogens or from one to three same or different substituents selected from the group consisting of C(O)NR$^{55}$R$^{56}$, hydroxy, cyano and XR$^{57}$;

E is selected from the group consisting of (C$_{1-6}$)alkyl, (C$_{3-7}$)cycloalkyl and (C$_{2-6}$)alkenyl; wherein said (C$_{1-6}$)alkyl and (C$_{2-6}$)alkenyl are independently optionally substituted with a member selected from the group consisting of phenyl, heteroaryl, SMe, Ph, —C(O)NR$^{56}$R$^{57}$, C(O)R$^{57}$, SO$_2$(C$_{1-6}$)alkyl and SO$_2$Ph; wherein heteroaryl is a monocyclic system which contains from 3 to 7 ring atoms, including from 1 to 4 heteroatoms;

F is selected from the group consisting of (C$_{1-6}$)alkyl, (C$_{3-7}$)cycloalkyl, aryl, heteroaryl, heteroalicyclic, hydroxy, (C$_{1-6}$)alkoxy, aryloxy, (C$_{1-6}$)thioalkoxy, cyano, halogen, nitro, —C(O)R$^{57}$, benzyl, —NR$^{42}$C(O)—(C$_{1-6}$)alkyl, —NR$^{42}$C(O)—(C$_{3-6}$)cycloalkyl, —NR$^{42}$C(O)-aryl, —NR$^{42}$C(O)-heteroaryl, —NR$^{42}$C(O)-heteroalicyclic, a 4, 5, or 6 membered ring cyclic N-lactam, —NR$^{42}$S(O)$_2$—(C$_{1-6}$)alkyl, —NR$^{42}$S(O)$_2$—(C$_{3-6}$)cycloalkyl, —NR$^{42}$S(O)2-aryl, —NR$^{42}$S(O)$_2$-heteroaryl, —NR$^{42}$S(O)2-heteroalicyclic, S(O)$_2$(C$_{1-6}$)alkyl, S(O)$_2$aryl, —S(O)2 NR$^{42}$R$^{43}$, NR$^{42}$R$^{43}$, (C$_{1-6}$)alkylC(O)NR$^{42}$R$^{43}$, C(O)NR$^{42}$R$^{43}$, NHC(O)NR$^{42}$R$^{43}$, OC(O)NR$^{42}$R$^{43}$, NHC(O)OR$^{54}$, (C$_{1-6}$)alkylNR$^{42}$R$^{43}$, COOR$^{54}$, and (C$_{1-6}$)alkylCOOR$^{54}$; wherein said (C$_{1-6}$)alkyl, (C$_{3-2}$)cycloalkyl, aryl, heteroaryl, heteroalicyclic, (C$_{1-6}$)alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

G is selected from the group consisting of (C$_{1-6}$)alkyl, (C$_{3-7}$)cycloalkyl, aryl, heteroaryl, heteroalicyclic, hydroxy, (C$_{1-6}$)alkoxy, aryloxy, cyano, halogen, nitro, —C(O)R$^{57}$, benzyl, —NR$^{48}$C(O)—(C$_{1-6}$)alkyl, —NR$^{48}$C(O)—(C$_{3-6}$)cycloalkyl, —NR$^{48}$C(O)-aryl, —NR$^{48}$C(O)-heteroaryl, —NR$^{48}$C(O)-heteroalicyclic, a 4, 5, or 6 membered ring cyclic N-lactam, —NR$^{48}$S(O)$_2$—(C$_{1-6}$)alkyl, —NR$^{48}$S(O)$_2$—(C$_{3-6}$)cycloalkyl, —NR$^{48}$S(O)2-aryl, —NR$^{48}$S(O)$_2$-heteroaryl, —NR$^{48}$S(O)2-heteroalicyclic, sulfinyl, sulfonyl, sulfonamide, NR$^{48}$R$^{49}$, (C$_{1-6}$)alkyl C(O)NR$^{48}$R$^{49}$, C(O)NR$^{48}$R$^{49}$, NHC(O)NR$^{48}$R$^{49}$, OC(O)NR$^{48}$R$^{49}$, NHC(O)OR$^{54'}$, (C$_{1-6}$)alkylNR$^{48}$R$^{49}$, COOR$^{54}$ and (C$_{1-6}$)alkylCOOR$^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

R$^7$ is selected from the group consisting of (C$_{1-6}$)alkyl, (C$_{2-6}$)alkenyl, (C$_{3-7}$)cycloalkyl, aryl, heteroaryl, and heteroalicyclic; wherein said aryl, heteroaryl, and heteroalicyclic are optionally substituted with one to three same or different halogens or with from one to three same or different substituents selected from the group F;

wherein for R$^7$, R$^8$, R$^{8a}$, R$^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

R$^8$ is selected from the group consisting of hydrogen, (C$_{1-6}$)alkyl, (C$_{3-7}$)cycloalkyl, (C$_2$-6)alkenyl, (C$_{3-7}$)cycloalkenyl, (C$_{2-6}$)alkynyl, aryl, heteroaryl, and heteroalicyclic; wherein said (C$_{1-6}$)alkyl, (C$_{3-7}$)cycloalkyl, (C$_{2-6}$)alkenyl, (C$_{3-7}$)cycloalkenyl, (C$_{2-6}$)alkynyl, aryl, heteroaryl, and heteroalicyclic are optionally substituted with one to six same or different halogens or from one to five same or different substituents selected from the group F or (C$_{1-6}$)alkyl, (C$_{3-6}$)cycloalkyl, cyano, phenyl, aryl, heteroaryl, heteroalicyclic, hydroxy, (C$_{1-6}$)alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

R$^{8a}$ is a member selected from the group consisting of aryl, heteroaryl, and heteroalicyclic; wherein each member is independently optionally substituted with one to six same or different halogens or from one to five same or different substituents selected from the group F;

R$^{8b}$ is selected from the group consisting of hydrogen, (C$_{1-6}$)alkyl and phenyl;

X is selected from the group consisting of CR$_1$R$_2$, NH or NCH$_3$, O, and S;

R$^{40}$ and R$^{41}$ are independently selected from the group consisting of (a) hydrogen; (b) (C$_{1-6}$)alkyl or (C$_{3-7}$)cycloalkyl substituted with one to three same or different halogens or from one to two same or different substituents selected from the group F or different functional groups: (C$_{1-6}$)alkyl, (C$_{3-6}$)cycloalkyl, cyano, phenyl, aryl, heteroaryl, heteroalicyclic, hydroxy, (C$_{1-6}$)alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and (c) $(C_{1-6})$alkoxy, aryl, heteroaryl or heteroalicyclic; or $R^{40}$ and $R^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is $C(O)NR^{40}R^{41}$, at least one of $R^{40}$ and $R^{41}$ is not selected from groups (a) or (b);

$R^{42}$ and $R^{43}$ are independently selected from the group consisting of hydrogen, $(C_{1-6})$alkyl, allyl, $(C_{1-6})$alkoxy, $(C_{3-7})$cycloalkyl, aryl, heteroaryl and heteroalicyclic; or $R^{42}$ and $R^{43}$ taken together with the nitrogen to which they are attached form a member selected from the group consisting of aziridine, azetidine, pyrrolidine, piperazine, 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to three same or different halogens or from one to two same or different substituents selected from the group G or different functional groups: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

$R^{46}$ is selected from the group consisting of H, phenyl, aryl, heteroaryl and $(C_{1-6})$alkyl, $OR^{57}$, and $NR^{55}R^{56}$;

$R^{47}$ is selected from the group consisting of H, amino, hydroxyl, phenyl, aryl, heteroaryl and $(C_{1-6})$alkyl;

$R^{48}$ and $R^{49}$ are independently selected from the group consisting of hydrogen, $(C_{1-6})$alkyl, phenyl, aryl and heteroaryl;

$R^{50}$ is selected from the group consisting of H, $(C_{1-6})$alkyl, $(C_{3-6})$cycloalkyl, and benzyl; wherein each of said $(C_{1-6})$alkyl, $(C_{3-7})$cycloalkyl and benzyl are optionally substituted with one to three same or different $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl $R^{54}$ is selected from the group consisting of hydrogen and $(C_{1-6})$alkyl;

$R^{54'}$ is $(C_{1-6})$alkyl;

$R^{55}$ and $R^{56}$ are independently selected from the group consisting of hydrogen and $(C_{1-6})$alkyl; and $R^{57}$ is selected from the group consisting of hydrogen, $(C_{1-6})$alkyl, aryl, heteroaryl; and $A^1$ and $A^2$ are independently selected from hydrogen, $(C_{1-6})$alkyl, aryl, heteroaryl, $SO_2D^1$, $SO_2ND^2D^3$, $COD^4$, $COCOD^4$, $COOD^4$, $COND^5D^6$, $COCOND^5D^6$, $COCOOD^4$, $C(=ND^7)D^8$, $C(=ND^9)ND^{10}D^{11}$;

$A^1$ and $A^2$ can either never connect with each other, or conjoin to form a ring structure;

$D^1$, $D^2$, $D^3$, $D^4$, $D^5$, $D^6$, $D^7$, $D^8$, $D^9$, $D^{10}$, and $D^{11}$ are each independently selected from the group consisting of H, $C_1$-$C_{50}$ alkyl, $C_3$-$C_{50}$ cycloalkyl, $C_3$-$C_{50}$ alkenyl, $C_4$-$C_{50}$ cycloalkenyl, phenyl, heteroaryl, $C_3$-$C_{50}$ amide and $C_3$-$C_{50}$ ether; heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl; provided the carbon atoms which comprise the carbon-carbon double bond of said $C_3$-$C_{20}$ alkenyl or the carbon-carbon triple bond of said $C_3$-$C_{20}$ alkynyl are not the point of attachment to the nitrogen to which $D^2$, $D^3$, $D^5$, $D^6$, $D^7$, $D^9$, $D^{10}$, and $D^{11}$ is attached; wherein said $C_1$-$C_{50}$ alkyl, $C_3$-$C_{50}$ cycloalkyl, $C_3$-$C_{50}$ alkenyl, $C_4$-$C_{50}$ cycloalkenyl, aryl, phenyl, heteroaryl, $C_3$-$C_{50}$ amide and $C_3$-$C_{50}$ ether is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide and steroid, among which ether, peroxide, thioether, secondary amine, tertiary amine, ammonium, ester, ketone, amide, amidine, oxime, hydrazine can be either acyclic or cyclic;

Z is selected from the group of:
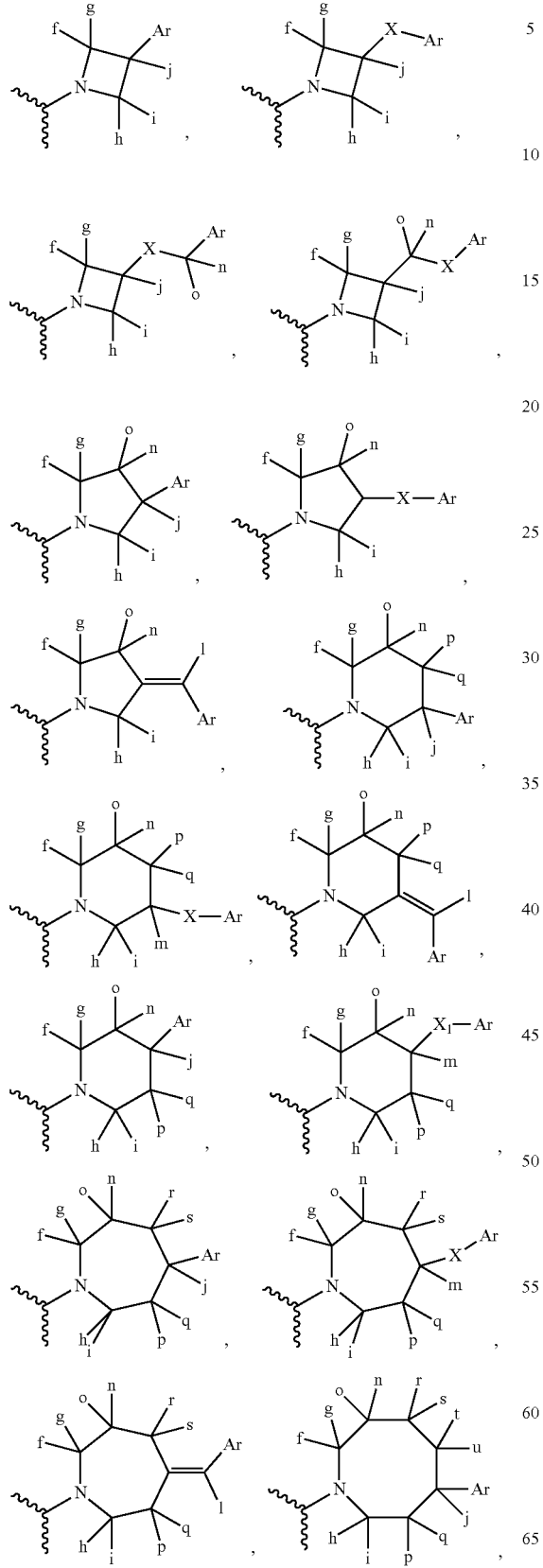
-continued
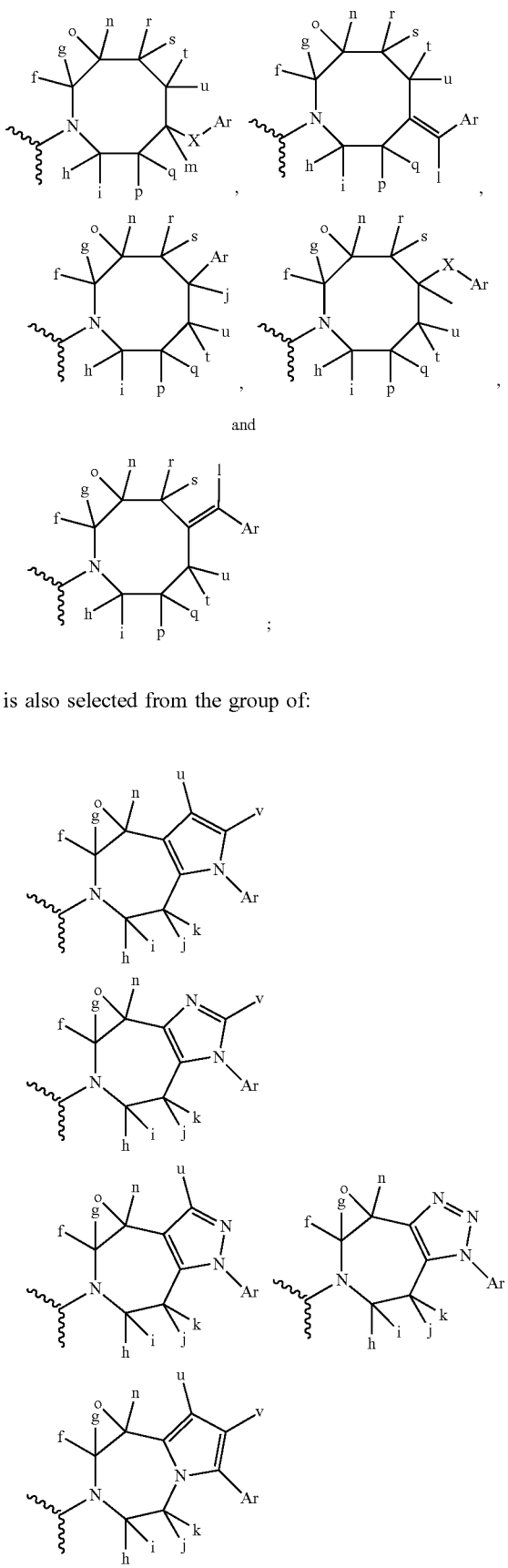
and
Z is also selected from the group of:

27
-continued
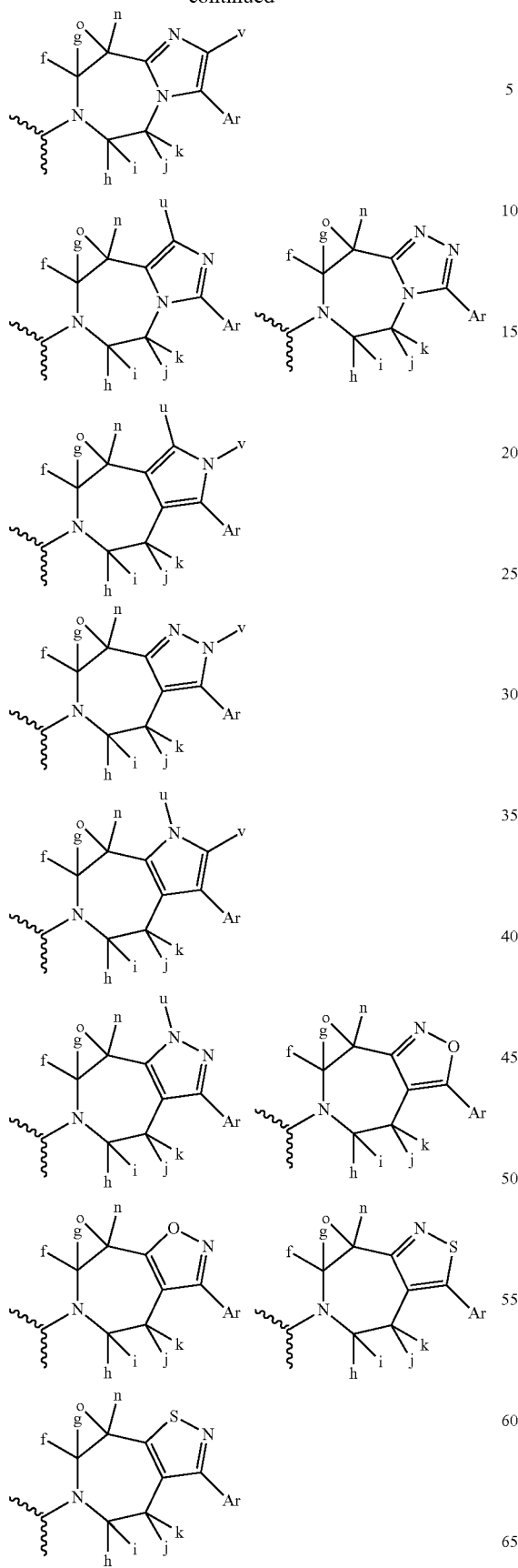
28
-continued
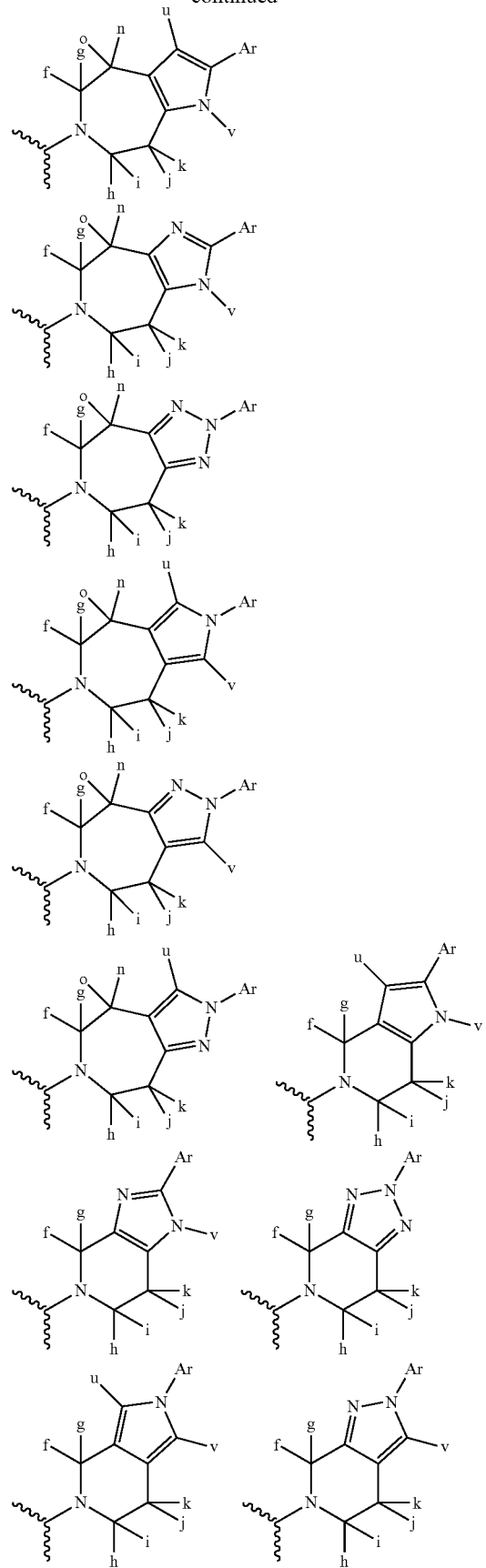

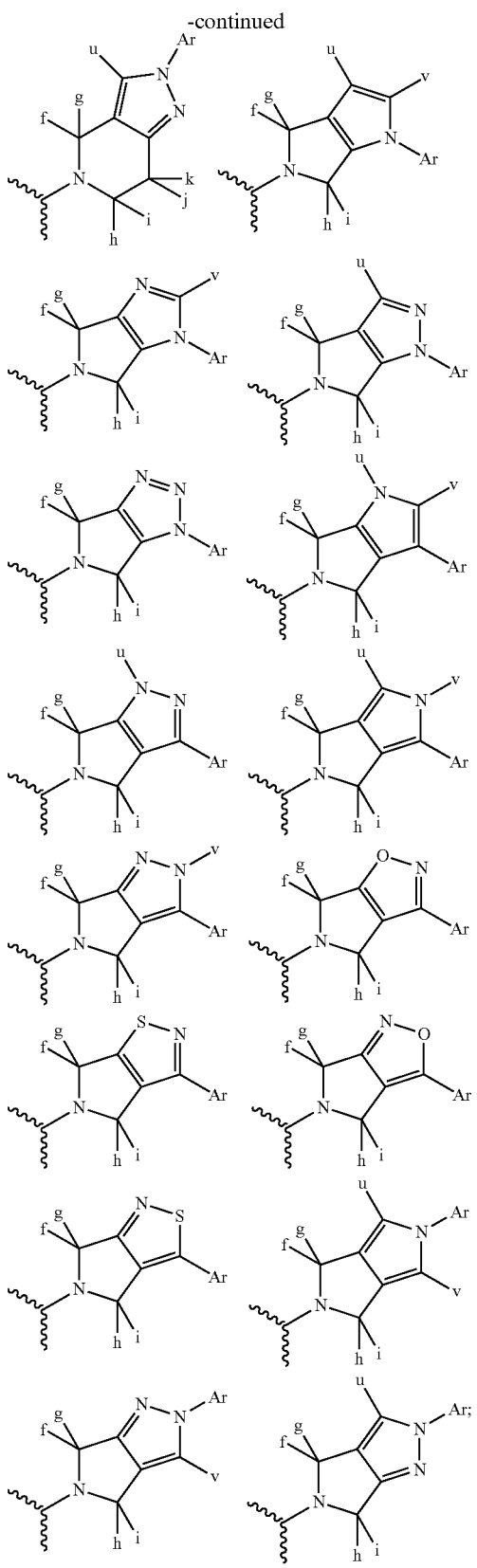

f and g are selected from the group consisting of H, (C₁-C₄) alkyl, and (C₃-C₆) cycloalkyl group, and wherein said alkyl or cycloalkyl group is optionally substituted with one to three substitutions selected from the group of F, OH, OR, $NR_1R_2$, COOR, and $CONR_1R_2$;

and wherein f and g can be connected by carbon, oxygen, nitrogen or sulfur atom to form a ring;

h and i are selected from the group consisting of H, (C₁-C₄) alkyl, and (C₃-C₆) cycloalkyl group. wherein said alkyl or cycloalkyl group is optionally substituted with one to three substitutions selected from the group of F, OH, OR, $NR_1R_2$, COOR, and $CONR_1R_2$;

and wherein h and i can be connected by a carbon, oxygen, nitrogen or sulfur atom to form a ring;

j is selected from the group consisting of H, F, (C₁-C₄) alkyl, and (C₃-C₆) cycloalkyl group, and wherein said alkyl or cycloalkyl group is optionally substituted with one to three substitutions selected from the group of F, OH, OR, $NR_1R_2$, COOR, and $CONR_1R_2$;

l is selected from the group consisting of hydrogen, $(C_{1-6})$ alkyl, $(C_{1-6})$alkynyl, $(C_{3-6})$ cycloalkyl, halogen, cyano, —$CONR^{32}R^{33}$, —$SO2\ R^{32}$, $COR^{32}$, $COOR^8$, tetrahydrofuryl, pyrrolidinyl, phenyl and heteroaryl; wherein said $(C_{1-6})$alkyl, $(C_{1-6})$alkynyl, phenyl and heteroaryl are each independently optionally substituted with one to three same or different members selected from the group U; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

m is selected from the group consisting of H, (C₁-C₄) alkyl optionally substituted with one to three substitutions selected from F, OH, OR, $NR_1R_2$, COOR, $CONR_1R_2$, (C₃-C₆) cycloalkyl optionally substituted with one to three substitutions selected from F, OH, OR, $NR_3R_4$, COOR, CON $R_3R_4$, OR, halogen (attached to carbon only), and Group X;

n, o, p, q, r, s, t and u are selected from the group consisting of H, F, (C₁-C₄) alkyl, and (C₃-C₆) cycloalkyl group, and wherein said alkyl or cycloalkyl group is optionally substituted with one to three substitutions selected from the group of F, OH, OR, $NR_1R_2$, COOR, and $CONR_1R_2$;

and wherein n, o, p, q, r, s, t and u can be connected by carbon, oxygen, nitrogen or sulfur atom to form a ring;

u and v are selected from the group consisting of H, OH, $NR_{1a}R_{2a}$, (C₁-C₄) alkyl optionally substituted with one to three substitutions selected from F, OH, OR, $NR_1R_2$, COOR, $CONR_1R_2$, (C₃-C₆) cycloalkyl optionally substituted with one to three substitutions selected from F, OH, OR, $NR_3R_4$, COOR, CON $R_3R_4$, OR, halogen (attached to carbon only), and Group X;

$X_1$ is selected from the group consisting of NH or $NCH_3$, O, and S;

Ar is selected from the group consisting of phenyl and heteroaryl; wherein said phenyl and heteroaryl are independently optionally substituted with one to three same or different halogens or from one to three same or different substituents selected from Group Y; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group U is selected from the group consisting of $(C_{1-6})$alkyl, $(C_{3-6})$cycloalkyl cyano, trimethylsilyl, phenyl, heteroaryl, heteroalicyclic, hydroxy, $(C_{1-6})$alkoxy, halogen, benzyl, —$NR^{42}C(O)$—$(C_{1-6})$alkyl, —$NR^{42}R^{43}$, —C(O) $NR^{42}R^{243}$, morpholino, nitro, —$S(C_{1-6})$alkyl, —SPh, $NR^{42}S(O)_2$-alkyl, piperazinyl, N-Me piperazinyl, $(CH2)_nCOOR^{54}$ and —$CONR^{42}R^{43}$; wherein said $(C_{1-6})$ alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

Group X is selected from the group consisting of phenyl and heteroaryl; wherein said phenyl and heteroaryl are independently optionally substituted with one to three same or different halogens or from one to three same or different substituents selected from Group D; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group Y is selected from the group consisting of OH, OR, $NR_1R_2$, CN, COOR, $CONR_1R_2$, $(C_1-C_4)$ alkyl, $(C_3-C_6)$ cycloalkyl, and wherein said alkyl or cycloalkyl group is optionally substituted with one to three substitutions selected from the group of F, OH, OR, $NR_1R_2$, COOR, and $CONR_1R_2$;

R, $R_1$, $R_2$, $R_{1a}$ and $R_{2a}$ are independently H, $(C_1-C_4)$ alkyl, $(C_3-C_6)$ cycloalkyl group; wherein said alkyl or cycloalkyl group is optionally substituted with one to three substitutions selected from F, OH, OR, $NR_3R_4$, COOR, CON $R_3R_4$;

and wherein $R_1$ and $R_2$ can be connected by carbon, oxygen, nitrogen or sulfur atom to form a ring; and $R_3$ and $R_4$ are independently H, $(C_1-C_4)$ alkyl, $(C_3-C_6)$ cycloalkyl group.

More preferred compounds of Formula I include those which are selected from the group of:

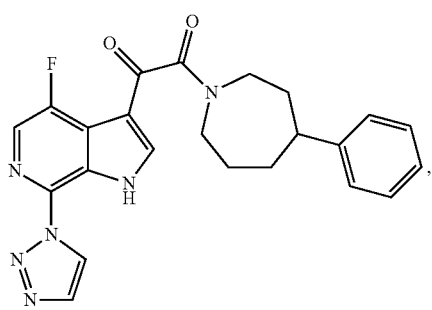

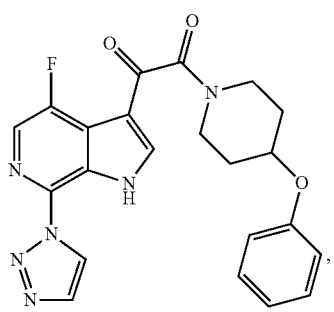

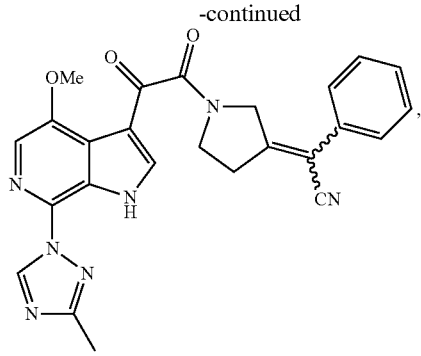

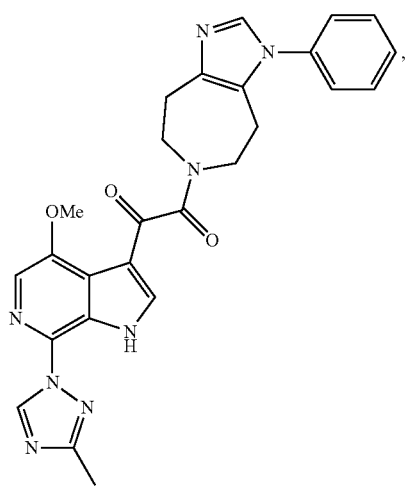

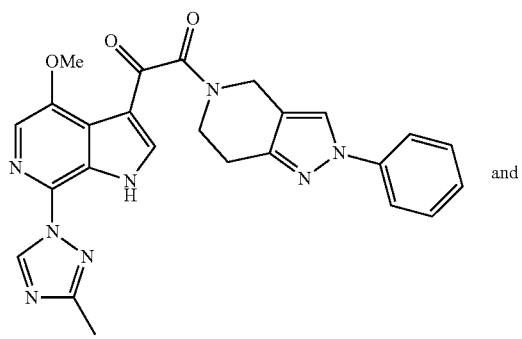

and

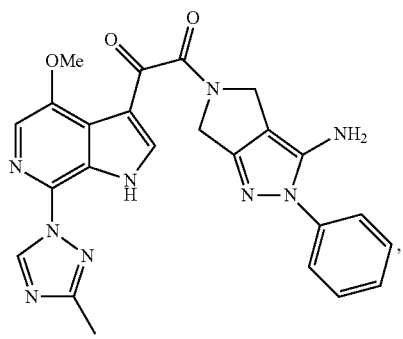 [SMILES: COc1cnc(-n2cnc(C)n2)c2[nH]cc(C(=O)C(=O)N3Cc4nn(-c5ccccc5)c(N)c4C3)c12]

including pharmaceutically acceptable salts thereof.

Of the foregoing,

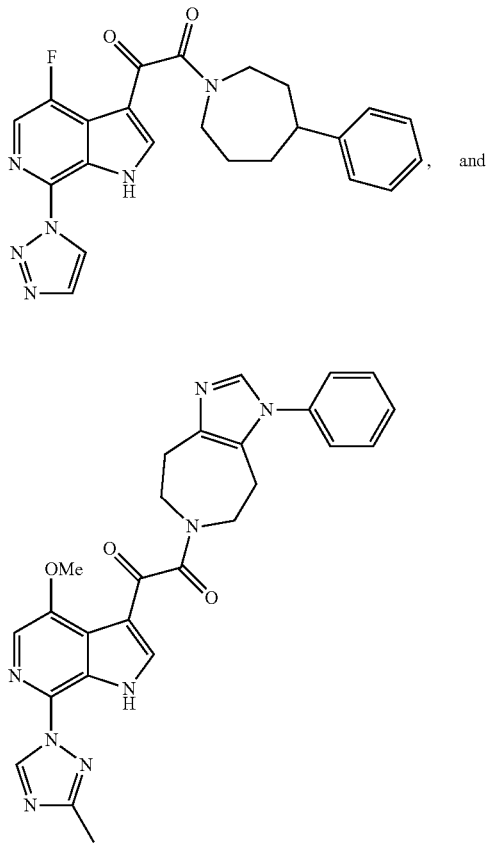

, and are even more preferred, including pharmaceutically acceptable salts thereof The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I, together with one or more pharmaceutically acceptable carriers, excipients and/or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients and/or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein can be administered orally to humans in a dosage range of 1 to 100 mg/kg body weight in divided doses, usually over an extended period, such as days, weeks, months, or even years. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more agents useful in the treatment of AIDS. For example, the compounds set forth herein may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| ANTIVIRALS | | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |

-continued

| Drug Name | Manufacturer | Indication |
| --- | --- | --- |
| Efavirenz (DMP 266, SUSTIVA ®) (—)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |

-continued

| Drug Name | Manufacturer | Indication |
| --- | --- | --- |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDS, protease inhibitor |
| FUZEON ® (Enfuvirtide or T-20) | Roche/Trimeris | HIV infection AIDS, viral Fusion inhibitor |
| LEXIVA ® (or Fosamprenavir calcium) | GSK/Vertex | HIV infection AIDS, viral protease inhibitor |
| SELZENTRY ® Maraviroc; (UK 427857) | Pfizer | HIV infection AIDS, (CCR5 antagonist, in development) |
| TRIZIVIR ® | GSK | HIV infection AIDS, (three drug combination) |
| Sch-417690 (vicriviroc) | Schering-Plough | HIV infection AIDS, (CCR5 antagonist, in development) |
| TAK-652 | Takeda | HIV infection AIDS, (CCR5 antagonist, in development) |
| GSK 873140 (ONO-4128) | GSK/ONO | HIV infection AIDS, (CCR5 antagonist, in development) |
| Integrase Inhibitor MK-0518 Raltegravir | Merck | HIV infection AIDS |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDS in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDS in development |
| CMX-157 Lipid conjugate of nucleotide tenofovir | Chimerix | HIV infection AIDS |
| GSK1349572 Integrase inhibitor | GSK | HIV infection AIDS |
| IMMUNOMODULATORS | | |
| AS-101 | Wyeth-Ayerst | AIDS |
| Bropirimine | Pharmacia Upjohn | Advanced AIDS |

-continued

| Drug Name | Manufacturer | Indication |
| --- | --- | --- |
| Acemannan | Carrington Labs, Inc. (Irving, TX) | AIDS, ARC |
| CL246, 738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |

-continued

| Drug Name | Manufacturer | Indication |
| --- | --- | --- |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. w/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein set forth may be used in combination with other HIV entry inhibitors. Examples of such HIV entry inhibitors are discussed in Drugs of the Future, 24(12):1355-1362 (1999); Cell, 9:243-246 (Oct. 29, 1999); and Drug Discovery Today, 5(5):183-194 (May 2000) and Meanwell, N. A. et al., "Inhibitors of the entry of HIV into host cells", Curr. Op. Drug Disc. Dev, 6(4):451-461 (2003). Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds set forth herein with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine. (The preparation of ddC, ddI and AZT are also described in EP 0 484 071.)

In such combinations, the compounds set forth herein and other active agents may be administered separately or in conjunction. In addition, the administration of one element may be prior to, concurrent to, or subsequent to the administration of other agent(s).

Methods of Synthesis

The present invention comprises compounds of Formula I, their pharmaceutical formulations, and their use in patients suffering from or susceptible to HIV infection. The compounds of Formula I include pharmaceutically acceptable salts thereof. The compounds may be made by methods available in the art, as well as those described after the Abbreviations and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations

One or more of the following abbreviations, most of which are conventional abbreviations well known to those skilled in the art, may be used throughout the description of the invention and the examples:
h=hour(s)
rt=room temperature mol=mole(s)
mmol=millimole(s)
g=gram(s)
mg=milligram(s)
mL=milliliter(s)
TFA=trifluoroacetic Acid
DCE=1,2-Dichloroethane
CH₂Cl₂=dichloromethane
TPAP=tetrapropylammonium perruthenate
THF=tetrahydrofuran
DEPBT=3-(diethoxyphosphoryloxy)-1,2,3-benzotriazin-4 (3H)-one
DMAP=4-dimethylaminopyridine
P-EDC=polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-diisopropylethylamine
MCPBA=meta-chloroperbenzoic acid
azaindole=1H-pyrrolo-pyridine
4-azaindole=1H-pyrrolo[3,2-b]pyridine
5-azaindole=1H-pyrrolo[3,2-c]pyridine
6-azaindole=1H-pyrrolo[2,3-c]pyridine
7-azaindole=1H-pyrrolo[2,3-b]pyridine
PMB=4-methoxybenzyl
DDQ=2,3-dichloro-5,6-dicyano-1,4-benzoquinone
OTf=trifluoromethanesulfonoxy
NMM=4-methylmorpholine
PIP-COPh=1-benzoylpiperazine
NaHMDS=sodium hexamethyldisilazide
EDAC=1-(3-dimethylaminopropyl)-3-ethylcarbodiimide
TMS=trimethylsilyl
DCM=dichloromethane
DCE=dichloroethane
MeOH=methanol
THF=tetrahydrofuran
EtOAc=ethyl acetate
LDA=lithium diisopropylamide
TMP-Li=2,2,6,6-tetramethylpiperidinyl lithium
DME=dimethoxyethane
DIBALH=diisobutylaluminum hydride
HOBT=1-hydroxybenzotriazole
CBZ=benzyloxycarbonyl
PCC=pyridinium chlorochromate
TBTU=O-(benzotriazol-1-yl)-N,N,N',N'-tetramethyluronium tetrafluoroborate
DEBPT=3-(diethoxyphosphoryloxy)-1,2,3-benzotriazin-4 (3H)-one
BOP=benzotriazole-1-yl-oxy-tris-(dimethylamino)-phosphoniumhexafluorophosphate Preparation of Compounds of Formula I Preparation of template A-CO—CO—Cl and A-CO—CO—OH has been described in detail in WO-00076521, WO-0162255, WO-0204440, WO-02062423, WO-02085301, WO-03068221 and US-2004/0063744.

Standard conditions such as reacting amine with acyl halide 1 (Scheme 1a) and carboxyl acid 3 (Scheme 1b) can be used to prepare the desired amide products. Some general references of these methodologies and directions for use are contained in "Comprehensive Organic Transformation" by Richard C. Larock, Wiley-VCH, New York, 1989, 972 (Carboxylic acids to amides), 979 (Acid halides to amides).

Scheme 1a

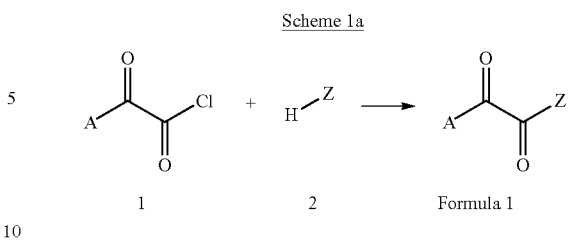

Scheme 1a depicts a general method for forming an amide from amine 2 and acyl chloride 1. An appropriate base (from catalytic to an excess amount) selected from sodium hydride, potassium carbonate, triethylamine, DBU, pyridine, DMAP or di-isopropyl ethyl amine was added into a solution of amine 2 and acyl chloride 1 in an appropriate solvent selected from dichloromethane, chloroform, benzene, toluene, THF, diethyl ether, dioxane, acetone, N,N-dimethylformamide or pyridine at room temperature. Then reaction was carried out at either room temperature or evaluated temperature up to 150° C. over a period of time (30 minutes to 48 hours) to afford the structure of Formula I. Some selected references involving such reactions include a) *Indian J. Chem., Sect B* 1990, 29, 1077; 2) *Chem. Sci.* 1998, 53, 1216; 3) *Chem. Pharm. Bull.* 1992, 40, 1481; 4) *Chem. Heterocycl. Compd.* 2002, 38, 539.

Scheme 1b

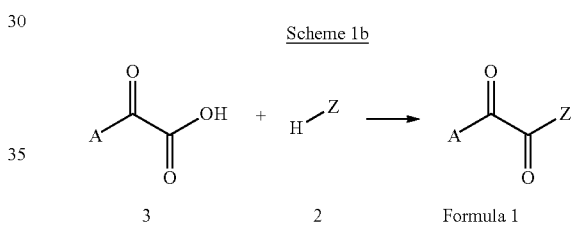

Alternatively, as shown in Scheme 1b, an amine 2 can be coupled with an acid 3 using standard amide bond or peptide bond forming coupling reagents. Many reagents for amide bond couplings are known by an organic chemist skilled in the art and nearly all of these are applicable for realizing coupled amide products. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU ((a) *J. Chem. Soc. Chem Comm.* 1994, 201; (b) *J. Am. Chem. Soc.* 1994, 116, 11580). Additionally, DEPBT (3-(diethoxyphosphoryloxy)-1,2,3-benzotriazin-4 (3H)-one) and N,N-diisopropylethylamine, commonly known as Hunig's base, represents another efficient method to form the amide bond and provide compounds of Formula I. DEPBT is either purchased from Aldrich or prepared according to the procedure described in *Organic Lett.*, 1999, 1, 91. Typically an inert solvent such as DMF or THF is used but other aprotic solvents could be used.

EXAMPLES

The following examples illustrate typical syntheses of the compounds of Formula I as described generally above. These examples are illustrative only and not intended to limit the invention in any way. The reagents and starting materials are readily available to one of ordinary skill in the art.

Chemistry Experimental

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($δ_H$ 7.26), CD$_3$OD ($δ_H$ 3.30), and DMSO-d6 ($δ_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

HPLC Method (i.e., Compound Isolation)

Compounds purified by preparative HPLC were diluted in methanol (1.2 mL) and purified using a Shimadzu LC-8A or LC-10A automated preparative HPLC system.

Typical Procedures and Characterization of Selected Examples:

Intermediate ACOCOOH or ACOCOCl:

Preparation of intermediate ACOCOOH or ACOCOCl was described in the previous published applications (W. Blair, et al. WO-200076521, O. Wallace, et al WO-200204440, T. Wang, et al. WO-200162255 and T. Wang, et al. WO-2002062423). Some examples of ACO-COOH are listed in below.

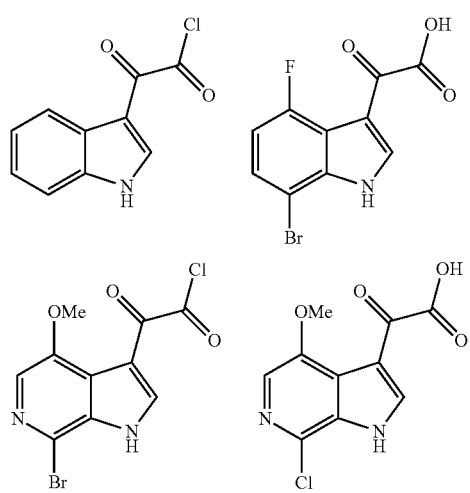

-continued

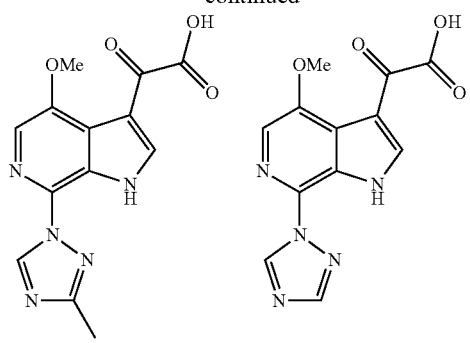

General Procedure to Prepare Formula I:

A)

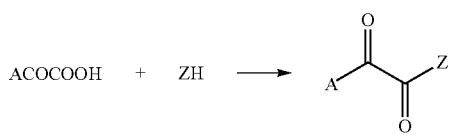

2-Keto acid (1 eq.), amine (1-5 eq.), 3-(diethoxyphosphoryloxy)-1,2,3-benzotriazin-4(3H)-one (DEPBT) or O-(1H-benzotriazol-1-yl)-N,N,N',N'-tetramethyluronium tetrafluoroborate (TBTU) (1-5 eq.) or (2-(7-Aza-1H-benzotriazole-1-yl)-1,1,3,3-tetramethyluronium hexafluorophosphate) (HATU) (1-5 eq.) and Hunig's Base or N-methyl morpholine (1-100 eq.) were combined in THF or DMF. The mixture was stirred at room temperature or 115° C. for 17 hours. THF or DMF was removed via evaporation at reduced pressure and the residue was partitioned between ethyl acetate and saturated NaHCO$_3$ aqueous solution. The aqueous layer was extracted with ethyl acetate. The organic phase was combined and dried over anhydrous MgSO$_4$. Concentration in vacuo provided a crude product, which was purified by titration, or recrystallization, or silica gel column chromatography, or Shimadzu automated preparative HPLC System.

B)

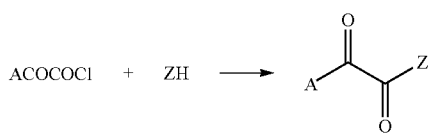

2-Keto acyl chloride (1 eq.), amine (1-5 eq.) and Hunig's Base or Et$_3$N (1-100 eq.) were combined in THF or DMF. The mixture was stirred at room temperature or 115° C. for 17 hours. THF or DMF was removed via evaporation at reduced pressure and the residue was partitioned between ethyl acetate and saturated NaHCO$_3$ aqueous solution. The aqueous layer was extracted with ethyl acetate. The organic phase was combined and dried over anhydrous MgSO$_4$. Concentration in vacuo provided a crude product, which was purified by titration, or recrystallization, or silica gel column chromatography, or Shimadzu automated preparative HPLC System.

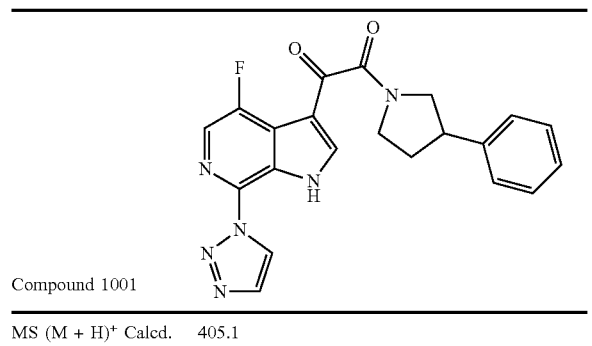

Compound 1001

| | |
|---|---|
| MS (M + H)+ Calcd. | 405.1 |
| MS (M + H)+ Observ. | 405.2 |
| Retention Time | 3.33 min |
| LC Condition | |
| Solvent A | 5% Water:95% Methanol:0.1% TFA |
| Solvent B | 95% Water:5% Methanol:0.1% TFA |
| Start % B | 0 |
| Final % B | 100 |
| Gradient Time | 4 min |
| Flow Rate | 4 mL/min |
| Wavelength | 220 |
| Solvent Pair | Water-Methanol-TFA |
| Column | PHENOMENEX-LUNA 4.6 × 50 mm S10 |

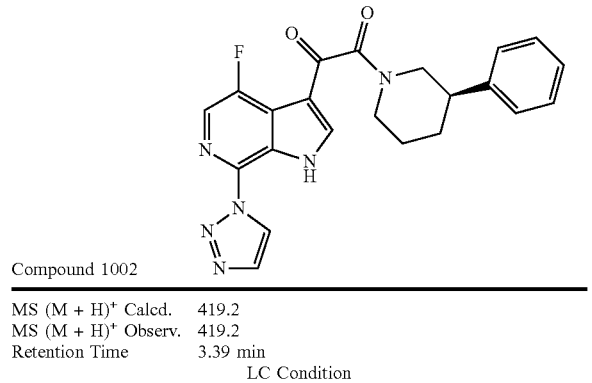

Compound 1002

| | |
|---|---|
| MS (M + H)+ Calcd. | 419.2 |
| MS (M + H)+ Observ. | 419.2 |
| Retention Time | 3.39 min |
| LC Condition | |
| Solvent A | 5% Water:95% Methanol:0.1% TFA |
| Solvent B | 95% Water:5% Methanol:0.1% TFA |
| Start % B | 0 |
| Final % B | 100 |
| Gradient Time | 4 min |
| Flow Rate | 4 mL/min |
| Wavelength | 220 |
| Solvent Pair | Water-Methanol-TFA |
| Column | PHENOMENEX-LUNA 4.6 × 50 mm S10 |

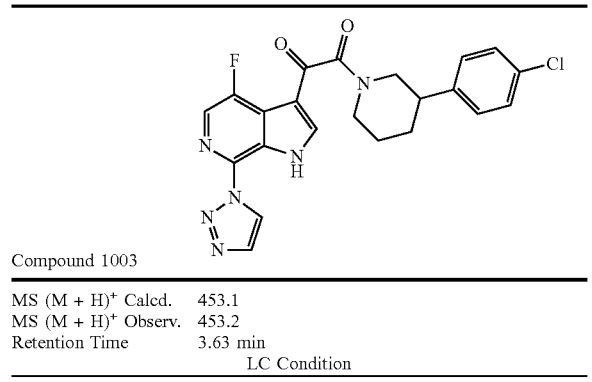

Compound 1003

| | |
|---|---|
| MS (M + H)+ Calcd. | 453.1 |
| MS (M + H)+ Observ. | 453.2 |
| Retention Time | 3.63 min |
| LC Condition | |
| Solvent A | 5% Water:95% Methanol:0.1% TFA |
| Solvent B | 95% Water:5% Methanol:0.1% TFA |
| Start % B | 0 |
| Final % B | 100 |
| Gradient Time | 4 min |

-continued

| | |
|---|---|
| Flow Rate | 4 mL/min |
| Wavelength | 220 |
| Solvent Pair | Water-Methanol-TFA |
| Column | PHENOMENEX-LUNA 4.6 × 50 mm S10 |

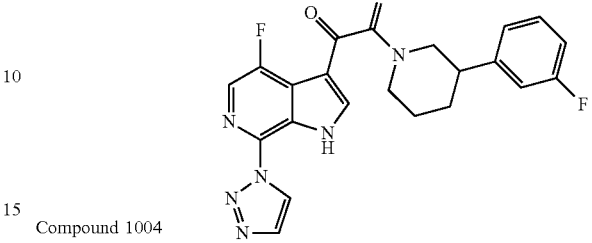

Compound 1004

| | |
|---|---|
| MS (M + H)+ Calcd. | 437.2 |
| MS (M + H)+ Observ. | 437.2 |
| Retention Time | 3.59 min |
| LC Condition | |
| Solvent A | 5% Water:95% Methanol:0.1% TFA |
| Solvent B | 95% Water:5% Methanol:0.1% TFA |
| Start % B | 0 |
| Final % B | 100 |
| Gradient Time | 4 min |
| Flow Rate | 4 mL/min |
| Wavelength | 220 |
| Solvent Pair | Water-Methanol-TFA |
| Column | PHENOMENEX-LUNA 4.6 × 50 mm S10 |

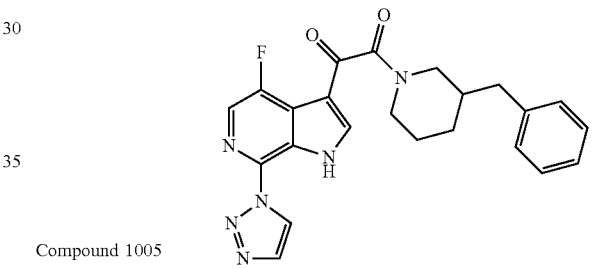

Compound 1005

| | |
|---|---|
| MS (M + H)+ Calcd. | 433.2 |
| MS (M + H)+ Observ. | 433.2 |
| Retention Time | 3.24 min |
| LC Condition | |
| Solvent A | 5% Water:95% Methanol:0.1% TFA |
| Solvent B | 95% Water:5% Methanol:0.1% TFA |
| Start % B | 0 |
| Final % B | 100 |
| Gradient Time | 4 min |
| Flow Rate | 4 mL/min |
| Wavelength | 220 |
| Solvent Pair | Water-Methanol-TFA |
| Column | PHENOMENEX-LUNA 4.6 × 50 mm S10 |

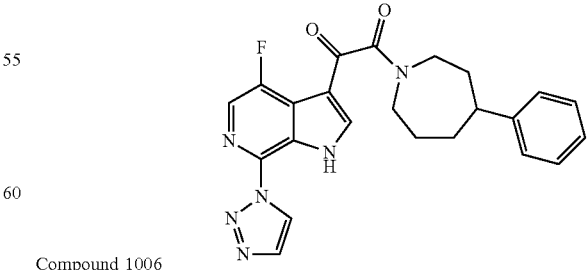

Compound 1006

| | |
|---|---|
| MS (M + H)+ Calcd. | 433.2 |
| MS (M + H)+ Observ. | 433.2 |
| Retention Time | 3.50 min |

-continued

| | |
|---|---|
| LC Condition | |
| Solvent A | 5% Water:95% Methanol:0.1% TFA |
| Solvent B | 95% Water:5% Methanol:0.1% TFA |
| Start % B | 0 |
| Final % B | 100 |
| Gradient Time | 4 min |
| Flow Rate | 4 mL/min |
| Wavelength | 220 |
| Solvent Pair | Water-Methanol-TFA |
| Column | PHENOMENEX-LUNA 4.6 × 50 mm S10 |

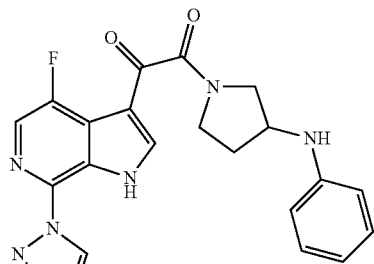

Compound 1007

| | |
|---|---|
| MS (M + H)+ Calcd. | 420.2 |
| MS (M + H)+ Observ. | 420.2 |
| Retention Time | 1.66 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 4 mL/min |
| Wavelength | 220 |
| Solvent Pair | Water-Methanol-TFA |
| Column | PHENOMENEX-LUNA 4.6 × 30 mm S10 |

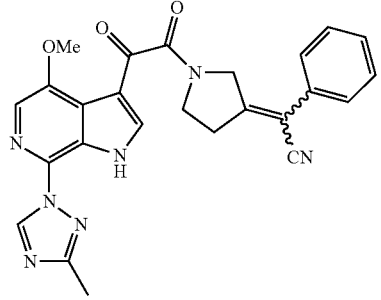

Compound 1008

| | |
|---|---|
| MS (M + H)+ Calcd. | 468.2 |
| MS (M + H)+ Observ. | 468.2 |
| Retention Time | 1.49 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 4 mL/min |
| Wavelength | 220 |
| Solvent Pair | ACN:Water:Ammonium Actetate |
| Column | Luna 4.6 × 50 mm S10 |

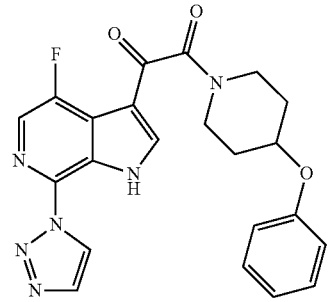

Compound 1009

| | |
|---|---|
| MS (M + H)+ Calcd. | 435.2 |
| MS (M + H)+ Observ. | 435.2 |
| Retention Time | 1.99 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 4 mL/min |
| Wavelength | 220 |
| Solvent Pair | Water-Methanol-TFA |
| Column | PHENOMENEX-LUNA 4.6 × 30 mm S10 |

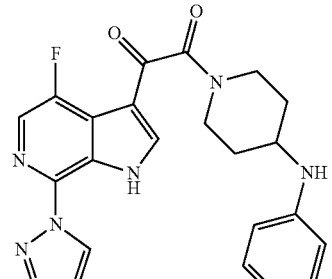

Compound 1010

| | |
|---|---|
| MS (M + H)+ Calcd. | 434.2 |
| MS (M + H)+ Observ. | 434.3 |
| Retention Time | 1.41 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 4 mL/min |
| Wavelength | 220 |
| Solvent Pair | Water-Methanol-TFA |
| Column | PHENOMENEX-LUNA 4.6 × 30 mm S10 |

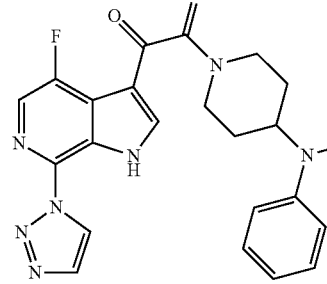

Compound 1011

| | |
|---|---|
| MS (M + H)+ Calcd. | 490.2 |
| MS (M + H)+ Observ. | 490.3 |
| Retention Time | 1.20 min |

53
-continued

| LC Condition | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 5 mL/min |
| Wavelength | 220 |
| Solvent Pair | ACN:Water:Ammonium Actetate |
| Column | PHENOMENEX-LUNA 3.0 × 50 mm S10 |

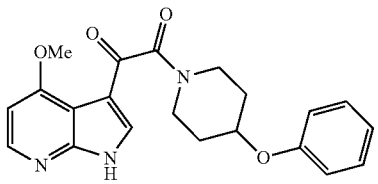 [SMILES: COc1ccnc2[nH]cc(C(=O)C(=O)N3CCC(Oc4ccccc4)CC3)c12]

Compound 1012

| | |
|---|---|
| MS (M + H)$^+$ Calcd. | 380.15 |
| MS (M + H)$^+$ Observ. | 380.15 |
| Retention Time | 1.2 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 2 min |
| Flow Rate | 5 mL/min |
| Wavelength | 220 |
| Solvent Pair | MeOH:Water:Ammonium Actetate |
| Column | XTERRA MS C18 7 μ 3.0 × 50 mm |

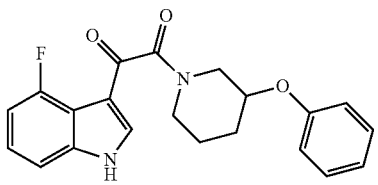 [SMILES: O=C(C(=O)N1CCCC(Oc2ccccc2)C1)c1c[nH]c2cccc(F)c12]

Compound 1016

| | |
|---|---|
| MS (M + H)$^+$ Calcd. | 367.1 |
| MS (M + H)$^+$ Observ. | 367.2 |
| Retention Time | 1.83 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 4 mL/min |
| Wavelength | 220 |
| Solvent Pair | Water-Methanol-TFA |
| Column | PHENOMENEX-LUNA 4.6 × 30 mm S10 |

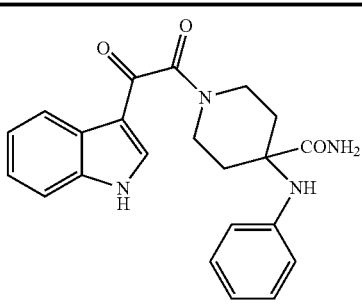

Compound 1017

| | |
|---|---|
| MS (M + Na)$^+$ Calcd. | 413.2 |
| MS (M + H)$^+$ Observ. | 413.5 |
| Retention Time | 1.51 min |

54
-continued

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | XTERRA ms C18 4.6 × 30 mm |

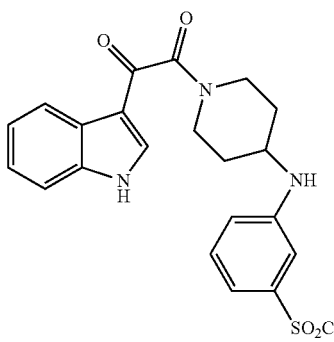

Compound 1018

| | |
|---|---|
| MS (M + H)$^+$ Calcd. | 480.1 |
| MS (M + H)$^+$ Observ. | 480.4 |
| Retention Time | 1.84 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | XTERRA ms C18 4.6 × 30 mm |

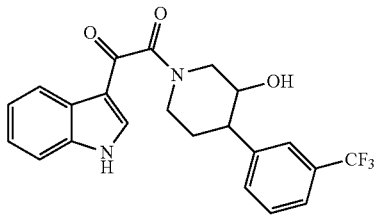 [SMILES: O=C(C(=O)N1CCC(c2cccc(C(F)(F)F)c2)C(O)C1)c1c[nH]c2ccccc12]

Compound 1019

| | |
|---|---|
| MS (M + Na)$^+$ Calcd. | 439.1 |
| MS (M + H)$^+$ Observ. | 439.4 |
| Retention Time | 1.77 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | XTERRA ms C18 4.6 × 30 mm |

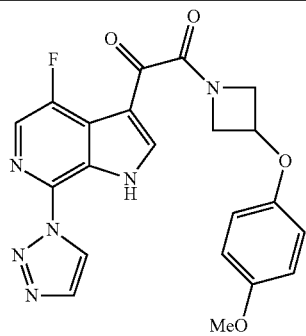

Compound 1020

| | |
|---|---|
| MS (M + H)+ Calcd. | 437.1 |
| MS (M + H)+ Observ. | 437.2 |
| Retention Time | 2.94 min |
| LC Condition | |
| Solvent A | 5% Water:95% Methanol:0.1% TFA |
| Solvent B | 95% Water:5% Methanol:0.1% TFA |
| Start % B | 0 |
| Final % B | 100 |
| Gradient Time | 4 min |
| Flow Rate | 4 mL/min |
| Wavelength | 220 |
| Solvent Pair | Water-Methanol-TFA |
| Column | PHENOMENEX-LUNA 4.6 × 50 mm S10 |

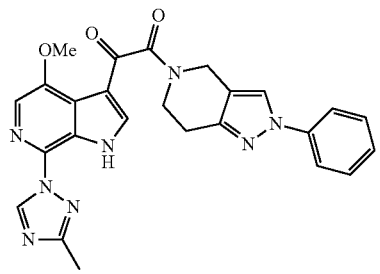 [SMILES: COc1cnc(-n2cnc(C)n2)c2[nH]cc(C(=O)C(=O)N3CCc4nn(-c5ccccc5)cc4C3)c12]

Compound 2002

| | |
|---|---|
| MS (M + H)+ Calcd. | 483.2 |
| MS (M + H)+ Observ. | 483.1 |
| Retention Time | 1.74 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 4 mL/min |
| Wavelength | 220 |
| Solvent Pair | Water-Methanol-TFA |
| Column | PHENOMENEX-LUNA 4.6 × 30 mm S10 |

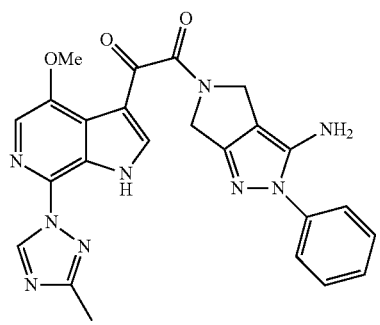 [SMILES: COc1cnc(-n2cnc(C)n2)c2[nH]cc(C(=O)C(=O)N3Cc4nn(-c5ccccc5)c(N)c4C3)c12]

Compound 2003

| | |
|---|---|
| MS (M + H)+ Calcd. | 484.2 |
| MS (M + H)+ Observ. | 484.4 |
| Retention Time | 1.72 min |

| LC Condition | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 4 mL/min |
| Wavelength | 220 |
| Solvent Pair | ACN:Water:Ammonium Actetate |
| Column | PHENOMENEX-LUNA 4.6 × 30 mm S10 |

Synthesis of Compound 2001:

Step 1:

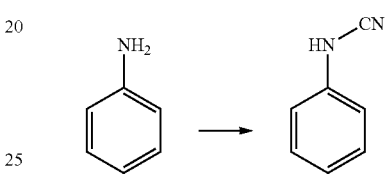

Cyanogen bromide (22 g) was slowly added to a stirred solution of aniline (10 g) in dry diethyl ether (150 mL) under nitrogen atmosphere at 0° C. The reaction mixture was stirred at room temperature for about 3 hours. The reaction mixture was filtered through celite bed and washed with diethyl ether (3×20 mL). The filtrate was concentrated under reduced pressure to give crude N-phenylcyanamide (8 g) as brown liquid, which was used for further reaction without purification. $^1$H NMR (DMSO-d$_6$): δ 6.97-7.03 (m, 3H), 7.30-7.36 (m, 2H), 10.13 (bs, 1H). MS: 117.2 (M−1)+.

Step 2:

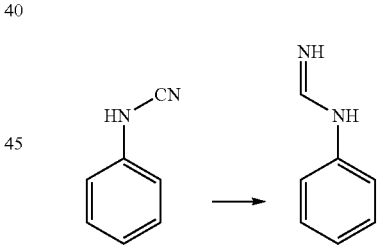

To a stirred solution of N-phenylcyanamide (8 g) in dry diethyl ether (50 mL), HCl in dry diethyl ether (20 mL) was slowly added under nitrogen atmosphere at 0° C. The reaction mixture was stirred at room temperature for about 30 minutes. The salt precipitated was filtered through Buckner funnel and washed with diethyl ether (3×20 mL) under nitrogen atmosphere. The HCl salt of N-phenylcyanamide was taken in dry ethanol (100 mL), slowly added palladium on carbon (2 g) under nitrogen atmosphere. The reaction mixture was allowed to stir under hydrogen atmosphere using bladder for 16 hours. After completion of the reaction, the reaction mixture was filtered through celite bed and washed with methanol (3×20 mL). The filtrate was concentrated under reduced pressure to afford the desired N-phenylformimidamide (7 g) as colorless liquid. MS: 119.1 (M−1)+.

Step 3:

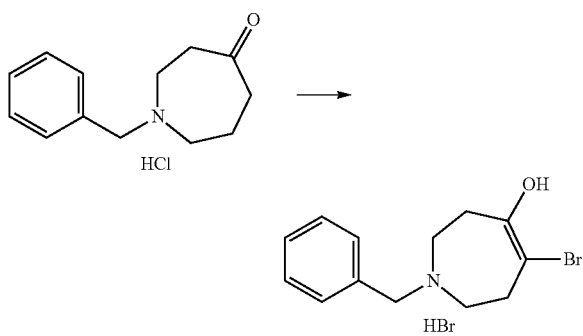

To a stirred solution of N-benzyl azepinone (5 g) in dry diethyl ether (50 mL), HCl in dry diethyl ether (20 mL) was slowly added under nitrogen atmosphere at 0° C. The reaction mixture was stirred at room temperature for about 30 minutes. The salt precipitated was filtered through Buckner funnel and washed with diethyl ether (3×20 mL) under nitrogen atmosphere. The HCl salt of N-benzyl azepinone was taken in acetic acid (15 mL) and HBr in acetic acid (15 mL) mixture, bromine (4 g) was then slowly added under nitrogen atmosphere. The reaction mixture was allowed to stir at room temperature for 2 hours. The reaction mixture was concentrated to remove volatiles under reduced pressure and the residue was diluted with diethyl ether (10 mL). Solid precipitated out, the solvent was decanted and the process was repeated three to four times. The solid was allowed to dry under reduced pressure to afford 1-benzyl-5-bromo-2,3,6,7-tetrahydro-1H-azepin-4-ol as a HBr salt (9 g), which was used further without any purification. $^1$H NMR (DMSO-$d_6$): δ 2.6-2.95 (m, 3H), 3.05-3.17 (m, 1H), 3.25-3.41 (m, 1H), 3.45-3.60 (m, 2H), 4.43-4.48 (m, 2H), 5.12-5.19 (m, 1H), 7.34-7.55 (m, 5H), 9.96-10.09 (bs, 1H). MS: 284.2 (M+1)$^+$.

Step 4:

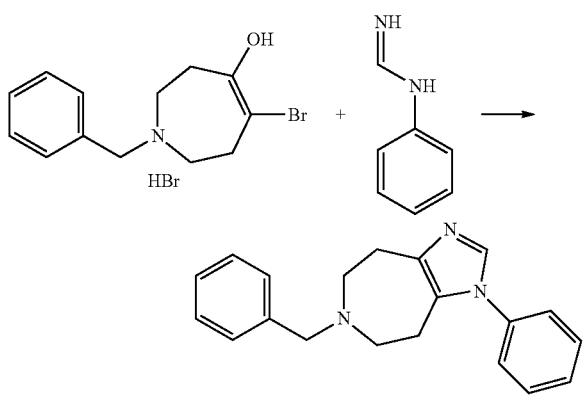

Sodium metal (1.6 g) was added slowly into dry ethanol (100 mL) under nitrogen atmosphere. The reaction mixture was stirred at room temperature until all the sodium metal dissolved, before N-phenylformimidamide (4 g) was added, followed by 1-benzyl-5-bromo-2,3,6,7-tetrahydro-1H-azepin-4-ol (10 g) under nitrogen atmosphere. The reaction mixture was stirred at 80° C. for 16 hours under nitrogen atmosphere before being cooled to room temperature. The reaction mixture was concentrated to remove ethanol under reduced pressure and the residue was diluted with ice cold water (50 mL). The product was extracted with ethyl acetate (3×50 mL) and the combined organic layer was washed with brine (50 mL). The organic layer was dried over anhydrous Na$_2$SO$_4$ and concentrated using rotary evaporator. The resulting crude was purified by column chromatography using MeOH/CHCl$_3$ (0.3:9.7) as eluent to afford 6-benzyl-1-phenyl-1,4,5,6,7,8-hexahydroimidazo[4,5-d]azepine (700 mg) as brown liquid. $^1$H NMR (DMSO-$d_6$): δ 2.59-2.62 (m, 2H), 2.75-2.83 (m, 6H), 3.76 (s, 2H), 7.24-7.30 (m, 1H), 7.32-7.38 (m, 2H), 7.44-7.50 (m, 4H), 7.50-7.52 (m, 1H), 7.52-7.54 (m, 2H), 7.59 (s, 1H). MS: 304.2 (M+1)$^+$.

Step 5:

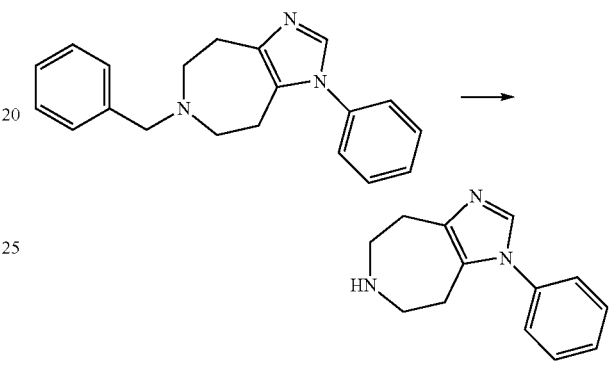

To a stirred solution of 6-benzyl-1-phenyl-1,4,5,6,7,8-hexahydroimidazo[4,5-d]azepine (0.65 g) in dry methanol (20 mL), palladium hydroxide (0.3 g) was slowly added under nitrogen atmosphere. The reaction mixture was allowed to stir at 3 kg pressure under hydrogen atmosphere for 16 hours. After completion of the reaction, the reaction mixture was filtered through celite bed and washed with methanol (3×20 mL). The filtrate was concentrated under reduced pressure to afford the desired 1-phenyl-1,4,5,6,7,8-hexahydroimidazo[4,5-d]azepine (160 mg) as brown solid. $^1$H NMR (DMSO-$d_6$): δ 2.57-2.61 (m, 2H), 2.79-2.85 (m, 2H), 3.56-3.61 (m, 2H), 3.79-3.85 (m, 2H), 7.35-7.38 (m, 2H), 7.44-7.51 (m, 3H), 7.65 (s, 1H). MS: 213.2 (M+1)$^+$.

Step 6:

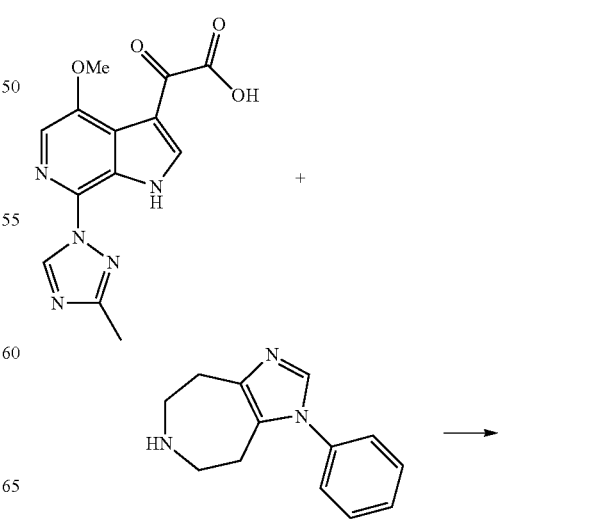

-continued

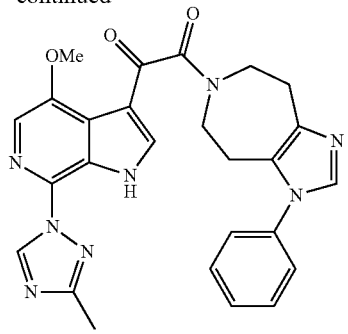

To a stirred solution of 2-(4-methoxy-7-(3-methyl-1H-1,2,4-triazol-1-yl)-1H-pyrrolo[2,3-c]pyridin-3-yl)-2-oxoacetic acid (200 mg) in dry DMF (5 mL), 1-phenyl-1,4,5,6,7,8-hexahydroimidazo[4,5-d]azepine (150 mg) in dry dichloromethane (5 mL), 2-chloro-1,3-dimethyl imidazolium chloride (54 mg) and iPr$_2$NEt (0.5 mL) were added. The reaction mixture was stirred at room temperature for 16 hours, before solvents were removed under reduced pressure. The resulting oil was diluted with dichloromethane (50 mL), washed with 10% NaHCO$_3$ (10 mL) and brine (10 mL). The organic layer was dried over anhydrous Na$_2$SO$_4$ and concentrated using rotary evaporator. The resulting crude was purified by column chromatography using MeOH/CHCl$_3$ (1.0:9.0) as eluent to afford compound 2001 (30 mg) as white solid. $^1$H NMR (400 MHz, DMSO-d6): δ 2.50 (s, 3H), 2.70-2.73 (t, 1H), 2.76-2.78 (t, 1H), 2.88-2.95 (m, 2H), 3.63-3.65 (t, 2H), 3.82-3.84 (m, 2H), 3.94 (s, 3H), 7.35-7.59 (m, 5H), 7.68 (s, 1H), 7.86-7.87 (d, 1H), 8.19-8.22 (d, 1H), 9.23 (s, 1H), 12.37 (bs, 1H). MS: 497.2 (M+1)$^+$.

Biology Data for the Examples

"μM" means micromolar;
"mL" means milliliter;
"μl" means microliter;
"mg" means milligram;

The materials and experimental procedures used to obtain the results reported in Table 1 are described below.

Cells:

Virus production—Human embryonic Kidney cell line, 293T (HEK 293T), was propagated in Dulbecco's Modified Eagle Medium (Invitrogen, Carlsbad, Calif.) containing 10% fetal bovine serum (FBS, Sigma, St. Louis, Mo.). The human T-cell leukemia cell MT2 (AIDS Research and Reference Reagent Program, Cat. 237) was propagated in RPMI 1640 (Invitrogen, Carlsbad, Calif.) containing 10% fetal bovine serum (FBS, Hyclone, Logan, Utah)

Virus infection—Single-round infectious reporter virus was produced by co-transfecting HEK 293T cells with plasmide expressing the HIV-1 LAI envelope along with a plasmid containing an HIV-1 LAI proviral cDNA with the envelope gene replaced by a firefly luciferase reporter gene (Chen et al., Ref 41). Transfections were performed using lipofectAMINE PLUS reagent as described by the manufacturer (Invitrogen, Carlsbad, Calif.).

Experimental Procedure

1. MT2 cells were plated in black, 384 well plates at a cell density of 5×10$^3$ cells per well in 25 μl RPMI 1640 containing 10% FBS.
2. Compound (diluted in dimethylsulfoxide and growth medium) was added to cells at 12.5 μl/well, so that the final assay concentration would be ≤50 nM.
3. 12.5 μl of single-round infectious reporter virus in Dulbecco's Modified Eagle Medium was added to the plated cells and compound at an approximate multiplicity of infection (MOI) of 0.01, resulting in a final volume of 50 μl per well.

4. Virus-infected cells were incubated at 37 degrees Celsius in a CO$_2$ incubator and harvested 72 h after infection.
5. Viral infection was monitored by measuring luciferase expression in the infected cells using a luciferase reporter gene assay kit (Steady-Glo, Promega, Madison, Wis.) as described by the manufacturer. Luciferase activity was then quantified by measuring luminescence using an EnVision Multilabel Plate Readers (PerkinElmer, Waltham, Mass.).
6. The percent inhibition for each compound was calculated by quantifying the level of luciferase expression in cells infected in the presence of each compound as a percentage of that observed for cells infected in the absence of compound and subtracting such a determined value from 100.
7. An EC$_{50}$ provides a method for comparing the antiviral potency of the compounds of the invention. The effective concentration for fifty percent inhibition (EC$_{50}$) was calculated with the Microsoft Excel Xlfit curve fitting software. For each compound, curves were generated from percent inhibition calculated at 10 different concentrations by using a four parameter logistic model (model 205). The EC$_{50}$ data for the compounds is shown in Table 2. Table 1 is the key for the data in Table 2.

TABLE 1

| Biological Data Key for EC$_{50}$ | |
|---|---|
| Compounds with EC$_{50}$ >0.5 μM | Compounds with EC$_{50}$ <0.5 μM |
| Group B | Group A |

TABLE 2
| Compd. Number | Structure | EC$_{50}$ Group from Table 1 |
|---|---|---|
| 1001 | 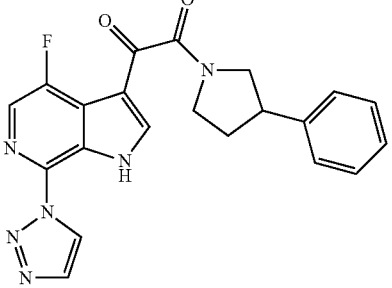 | A<br>38.15 nM |
| 1002 | 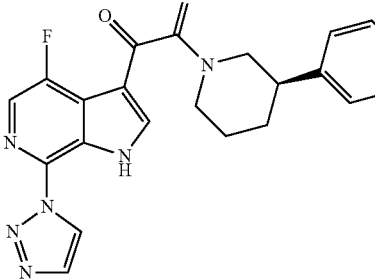 | A |
| 1003 | 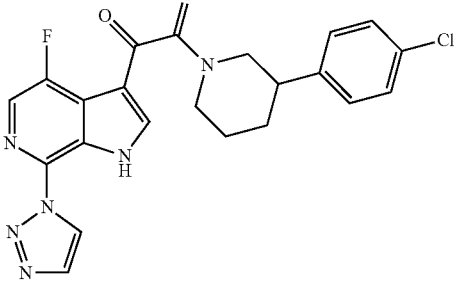 | B |
| 1004 | 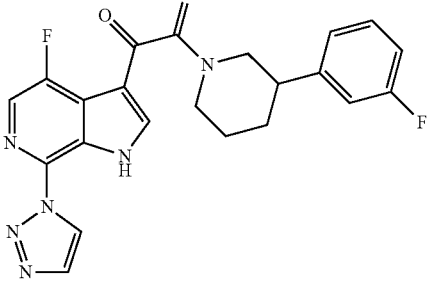 | B |
| 1005 | 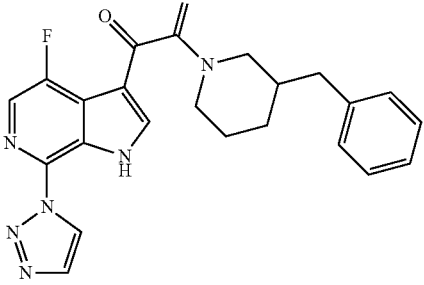 | B |

TABLE 2-continued

| Compd. Number | Structure | EC$_{50}$ Group from Table 1 |
|---|---|---|
| 1006 | 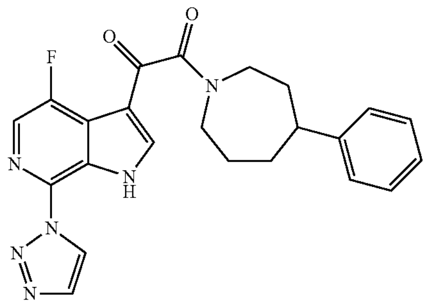 [SMILES: O=C(C(=O)N1CCCC(c2ccccc2)CC1)c1c[nH]c2c(-n3ccnn3)ncc(F)c12] | A |
| 1007 | 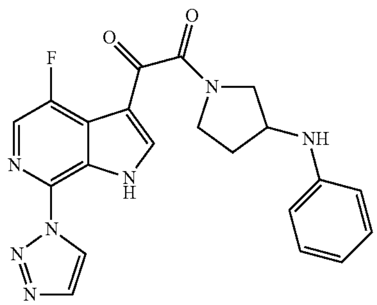 [SMILES: O=C(C(=O)N1CCC(Nc2ccccc2)C1)c1c[nH]c2c(-n3ccnn3)ncc(F)c12] | A |
| 1008 | 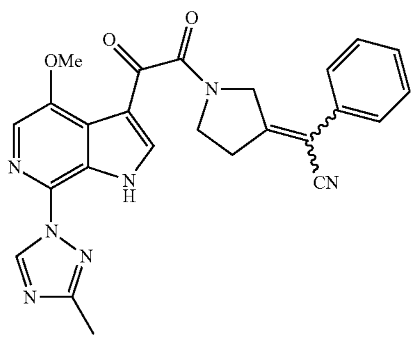 | A<br>18.92 nM |
| 1009 | 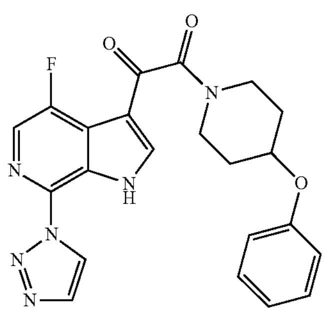 [SMILES: O=C(C(=O)N1CCC(Oc2ccccc2)CC1)c1c[nH]c2c(-n3ccnn3)ncc(F)c12] | A |
| 1010 | 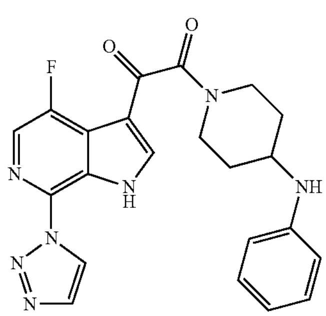 [SMILES: O=C(C(=O)N1CCC(Nc2ccccc2)CC1)c1c[nH]c2c(-n3ccnn3)ncc(F)c12] | A<br>41.80 nM |

TABLE 2-continued
| Compd. Number | Structure | EC$_{50}$ Group from Table 1 |
|---|---|---|
| 1011 | 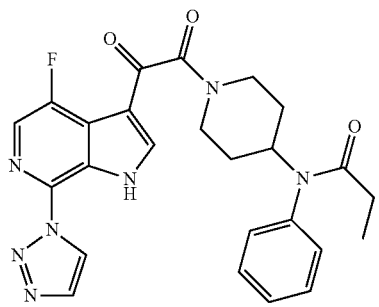 [SMILES: CCC(=O)N(c1ccccc1)C1CCN(C(=O)C(=O)c2c[nH]c3c(-n4ccnn4)ncc(F)c23)CC1] | A |
| 1012 | 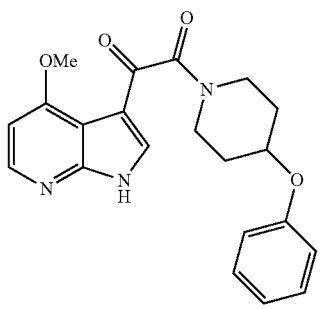 [SMILES: COc1ccnc2[nH]cc(C(=O)C(=O)N3CCC(Oc4ccccc4)CC3)c12] | A |
| 1013 | 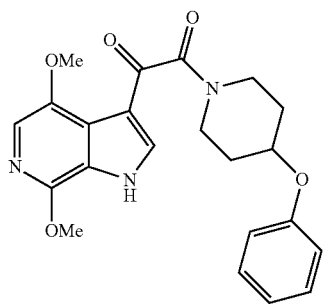 [SMILES: COc1ncc(OC)c2c(C(=O)C(=O)N3CCC(Oc4ccccc4)CC3)c[nH]c12] | B |
| 1014 | 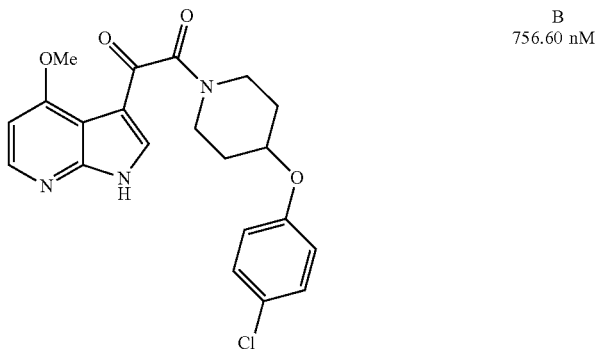 | B<br>756.60 nM |

TABLE 2-continued
| Compd. Number | Structure | EC$_{50}$ Group from Table 1 |
|---|---|---|
| 1015 | 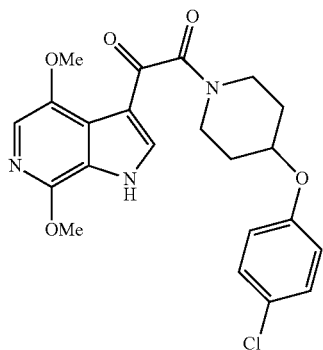 [SMILES: COc1ncc(OC)c2c(C(=O)C(=O)N3CCC(Oc4ccc(Cl)cc4)CC3)c[nH]c12] | B |
| 1016 | 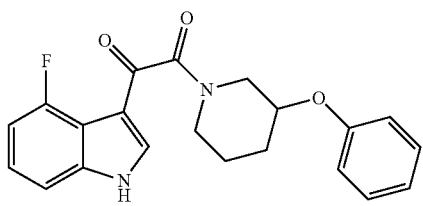 [SMILES: O=C(C(=O)N1CCCC(Oc2ccccc2)C1)c1c[nH]c2cccc(F)c12] | B |
| 1017 | 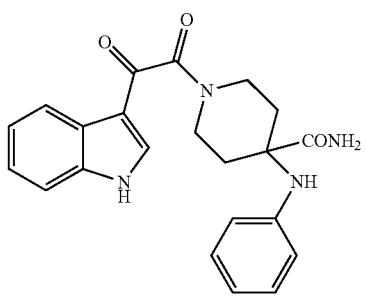 [SMILES: NC(=O)C1(Nc2ccccc2)CCN(C(=O)C(=O)c2c[nH]c3ccccc23)CC1] | B |
| 1018 | 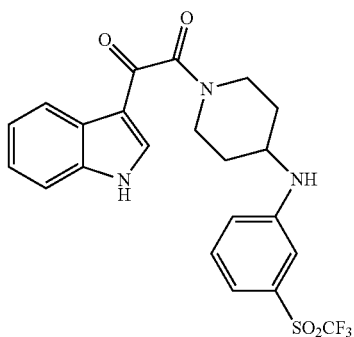 | B |
| 1019 | 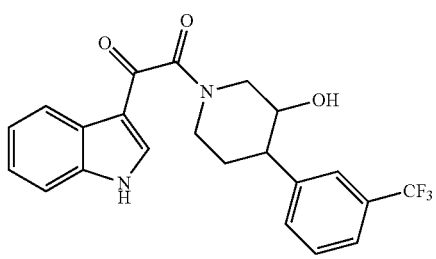 [SMILES: O=C(C(=O)N1CCC(c2cccc(C(F)(F)F)c2)C(O)C1)c1c[nH]c2ccccc12] | B |

TABLE 2-continued

| Compd. Number | Structure | EC$_{50}$ Group from Table 1 |
|---|---|---|
| 1020 | 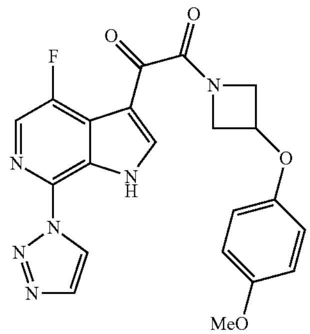 [SMILES: COc1ccc(OC2CN(C(=O)C(=O)c3c[nH]c4c(-n5ccnn5)ncc(F)c34)C2)cc1] | A |
| 2001 | 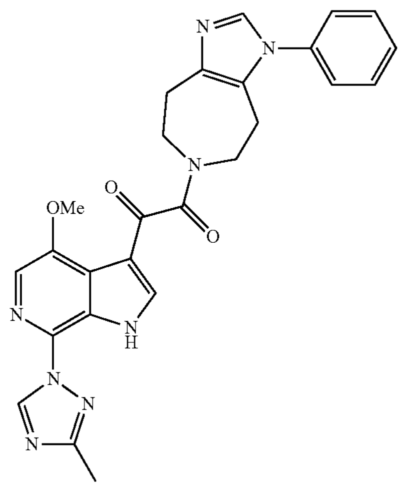 [SMILES: COc1cnc(-n2cnc(C)n2)c2[nH]cc(C(=O)C(=O)N3CCc4ncn(-c5ccccc5)c4CC3)c12] | A<br>0.09 nM |
| 2002 | 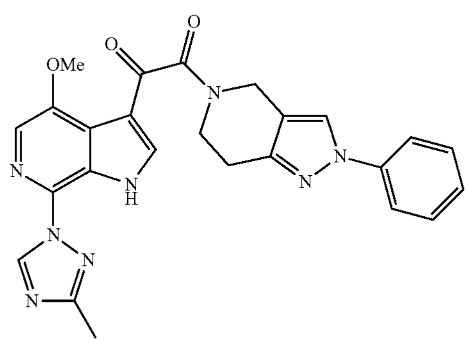 [SMILES: COc1cnc(-n2cnc(C)n2)c2[nH]cc(C(=O)C(=O)N3CCc4nn(-c5ccccc5)cc4C3)c12] | A<br>0.92 nM |
| 2003 | 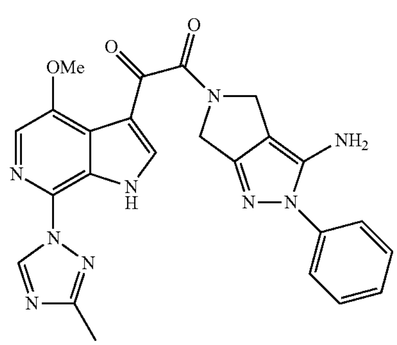 [SMILES: COc1cnc(-n2cnc(C)n2)c2[nH]cc(C(=O)C(=O)N3Cc4nn(-c5ccccc5)c(N)c4C3)c12] | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:
1. A compound which is selected from the group of:

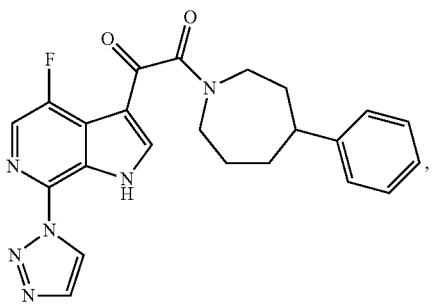

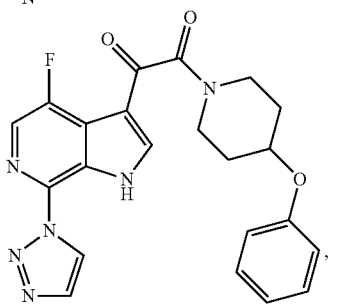

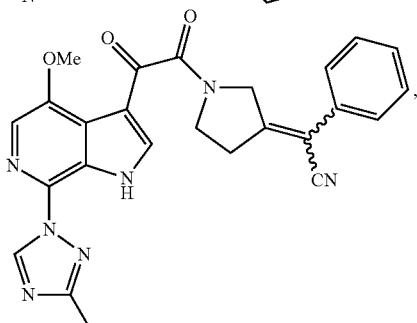

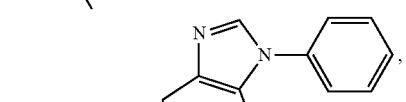

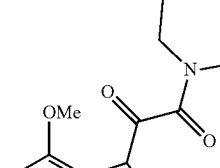

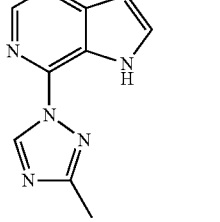

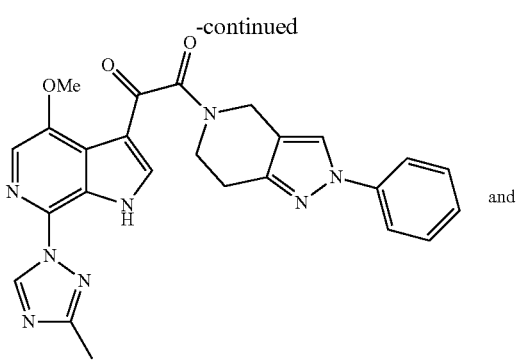

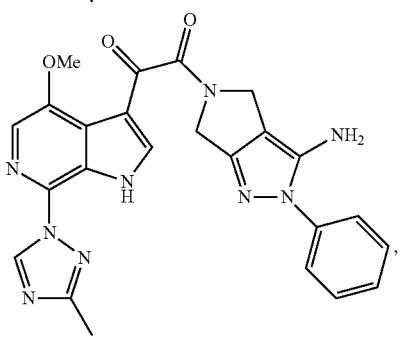

including pharmaceutically acceptable salts thereof.

2. A compound which is selected from

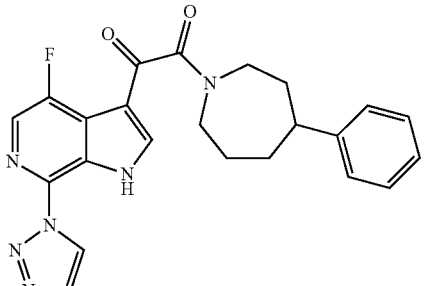

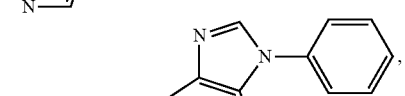

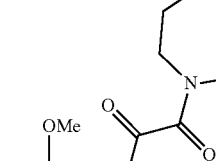

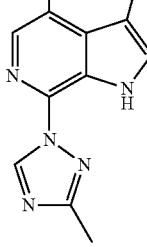

including pharmaceutically acceptable salts thereof.

3. A pharmaceutical composition which comprises an antiviral effective amount of one or more of the compounds as claimed in claim 1, together with one or more pharmaceutically acceptable carriers, excipients and/or diluents.

4. The pharmaceutical composition of claim 3, which additionally comprises an antiviral effective amount of an AIDS treatment agent.

5. A method for treating a mammal infected with the HIV virus comprising administering to said mammal an antiviral effective amount of a compound as claimed in claim 1, and one or more pharmaceutically acceptable carriers, excipients and/or diluents.

6. The method of claim 5, further comprising administering to said mammal an antiviral effective amount of an AIDS treatment agent.

* * * * *